(12) United States Patent
Tucker et al.

(10) Patent No.: US 8,128,964 B2
(45) Date of Patent: Mar. 6, 2012

(54) TRANSDERMAL PHARMACEUTICAL DELIVERY COMPOSITION

(75) Inventors: Arthur T. Tucker, London (GB); Nigel Benjamin, London (GB)

(73) Assignee: Queen Mary & Westfield College, London (GB)

( * ) Notice: Subject to any disclaimer, the term of this patent is extended or adjusted under 35 U.S.C. 154(b) by 970 days.

(21) Appl. No.: 10/363,439

(22) PCT Filed: Aug. 30, 2001

(86) PCT No.: PCT/GB01/03863
§ 371 (c)(1), (2), (4) Date: Jun. 16, 2003

(87) PCT Pub. No.: WO02/17881
PCT Pub. Date: Mar. 7, 2002

(65) Prior Publication Data
US 2004/0013747 A1    Jan. 22, 2004

(30) Foreign Application Priority Data
Aug. 30, 2000  (GB) .................................. 00213173

(51) Int. Cl.
*A01N 59/00*  (2006.01)
(52) U.S. Cl. ......... 424/718; 424/443; 424/444; 424/449
(58) Field of Classification Search .................. None
See application file for complete search history.

(56) References Cited

U.S. PATENT DOCUMENTS

| | | | |
|---|---|---|---|
| 5,648,101 A | | 7/1997 | Tawashi |
| 5,719,197 A | * | 2/1998 | Kanios et al. ............... 514/772.6 |
| 5,900,249 A | * | 5/1999 | Smith ............................ 424/443 |
| 6,103,275 A | * | 8/2000 | Seitz et al. ..................... 424/718 |

FOREIGN PATENT DOCUMENTS

| | | |
|---|---|---|
| JP | 58 000913 | 1/1983 |
| WO | WO 95 22335 | 8/1995 |
| WO | WO 98 47495 | 10/1998 |
| WO | WO 99 44622 | 9/1999 |

OTHER PUBLICATIONS

Merriam-Webster Online Dictionary, entry for "conjunction".*
Goodman and Gilman's The Pharmacological Basis of Therapeutics, 10$^{th}$ ed; Hardman, Limbird, Gilman, eds; pp. 845-853.*
Hakim et al., "Half-life of nitric oxide in aqueous solution with and without haemoglobin," Physiol. Meas. 17:267-277 (1996).
Hardwick et al., "A novel method for the delivery of nitric oxide to the skin of human subjects using a semi-permeable membrane," Clinical Science 100:395-400 (2001).
Liao, "Blood Feud: Keeping hemoglobin from nixing NO," Nature Medicine 8(12):1350-1351 (2002).
Reiter et al., "Cell-free hemoglobin limits nitric oxide bioavailability in sickle-cell disease," Nature Medicine 8(12): 1383-1389 (2002).
Tucker et al., "Study of a Combined percutaneous local anaesthetic and nitric-oxide generating system for venepuncture," Anaesthesia 57: 429-433 (2002).
Tucker et al., "Effect of nitric-oxide-generating system on microcirculatory blood flow in skin of patients with severe Raynaud's syndrome: a randomised trial," The Lancet, 354(13): 1670-1675 (1999).
Tucker et al., "Study of a combined percutaneous local anaesthetic and nitric oxide-generating system for venepuncture", Anaesthesia, 2002, 57, pp. 429-433.

* cited by examiner

*Primary Examiner* — Robert A Wax
*Assistant Examiner* — Hasan Ahmed
(74) *Attorney, Agent, or Firm* — Pepper Hamilton LLP

(57) ABSTRACT

A pharmaceutically delivery system is described comprising a pharmaceutically active agent and acidified nitrite as an agent to produce local production of nitric oxide at the skin surface. The dosage form may be in any pharmaceutically acceptable carrier means and comprises an acidifying agent adapted to reduce the pH at the environment. In one embodiment, a barrier consisting of a membrane allows diffusions of the anaesthetic and nitrite ions while preventing direct contact of the skin and acidifying agent.

22 Claims, 18 Drawing Sheets

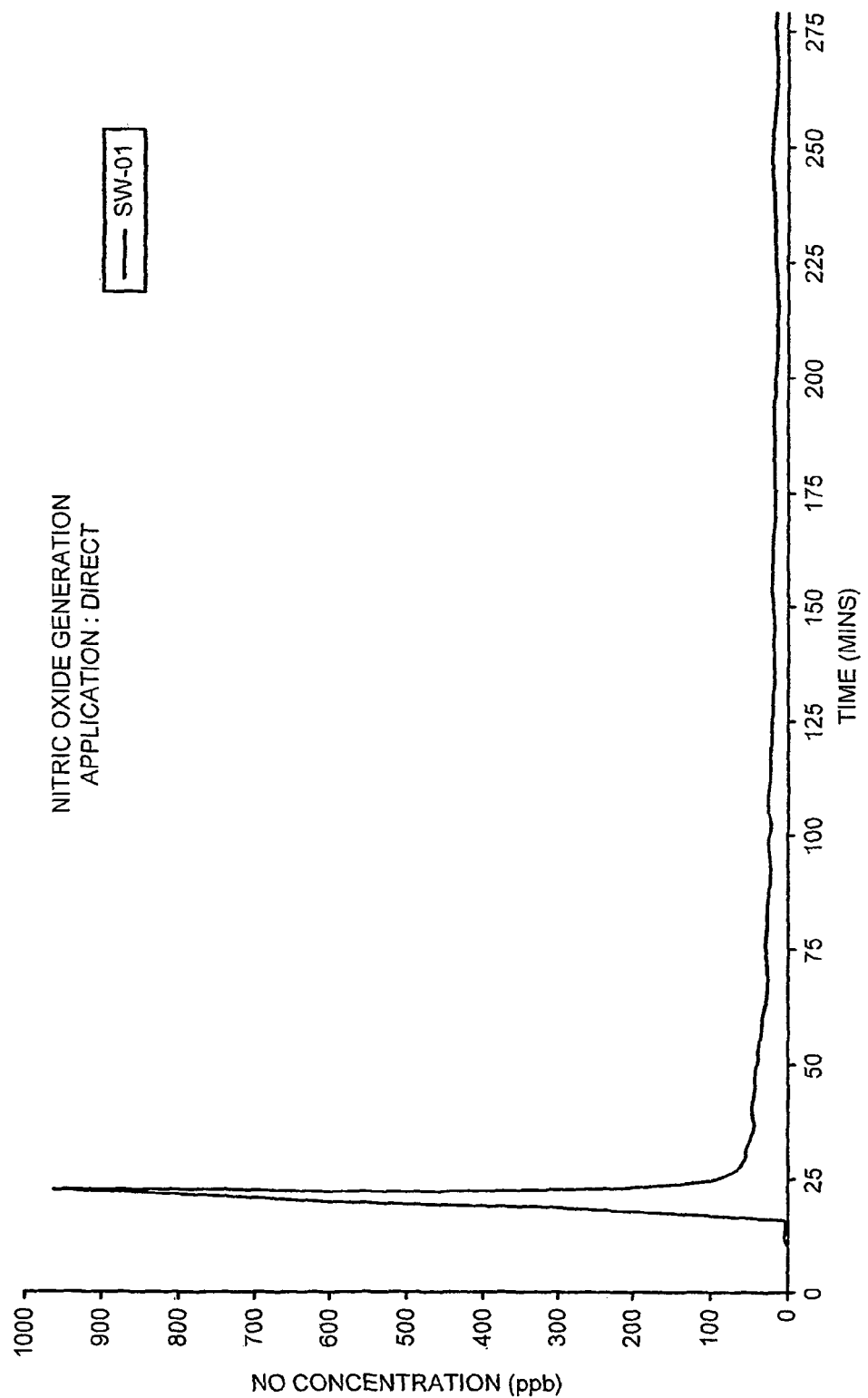

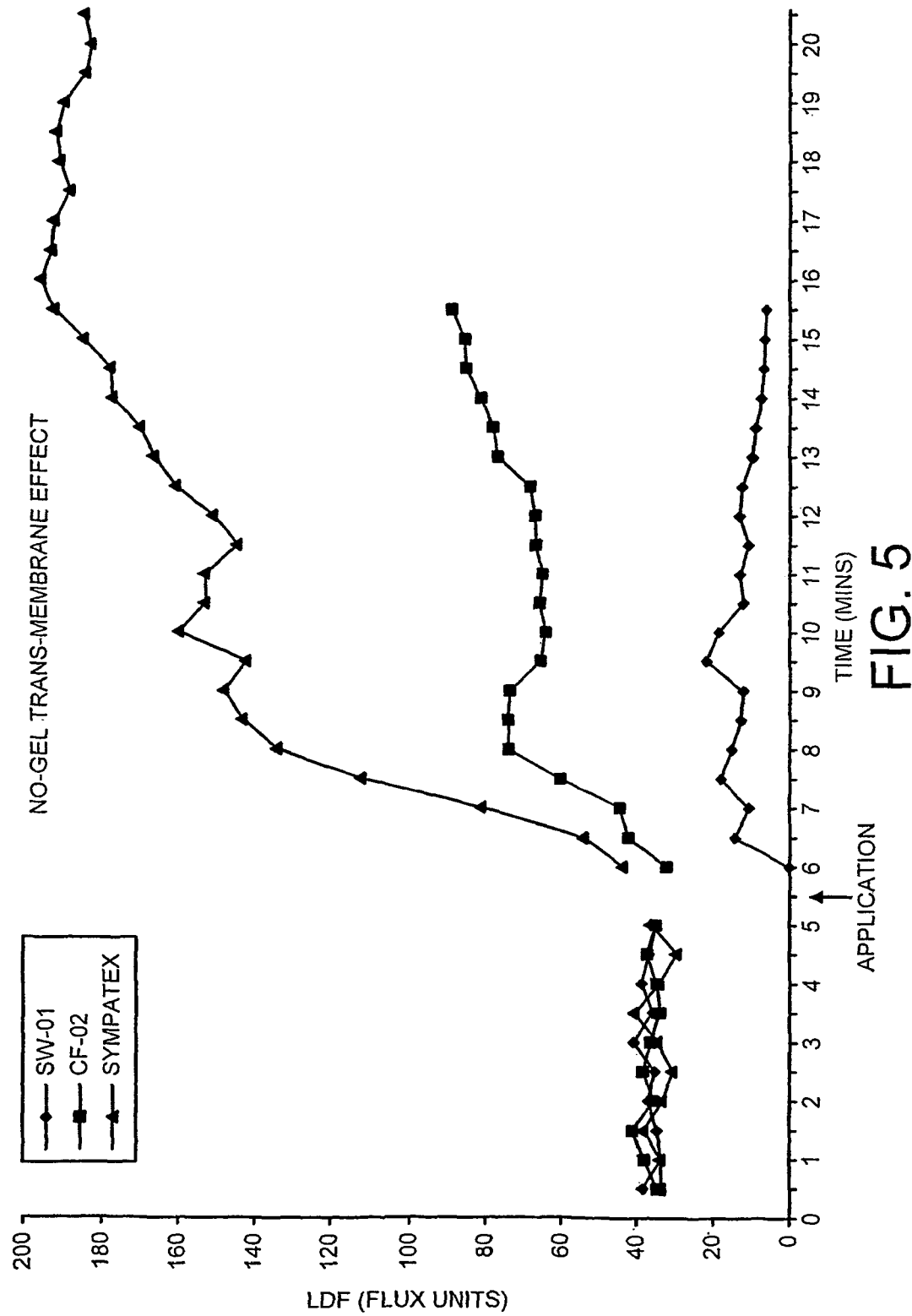

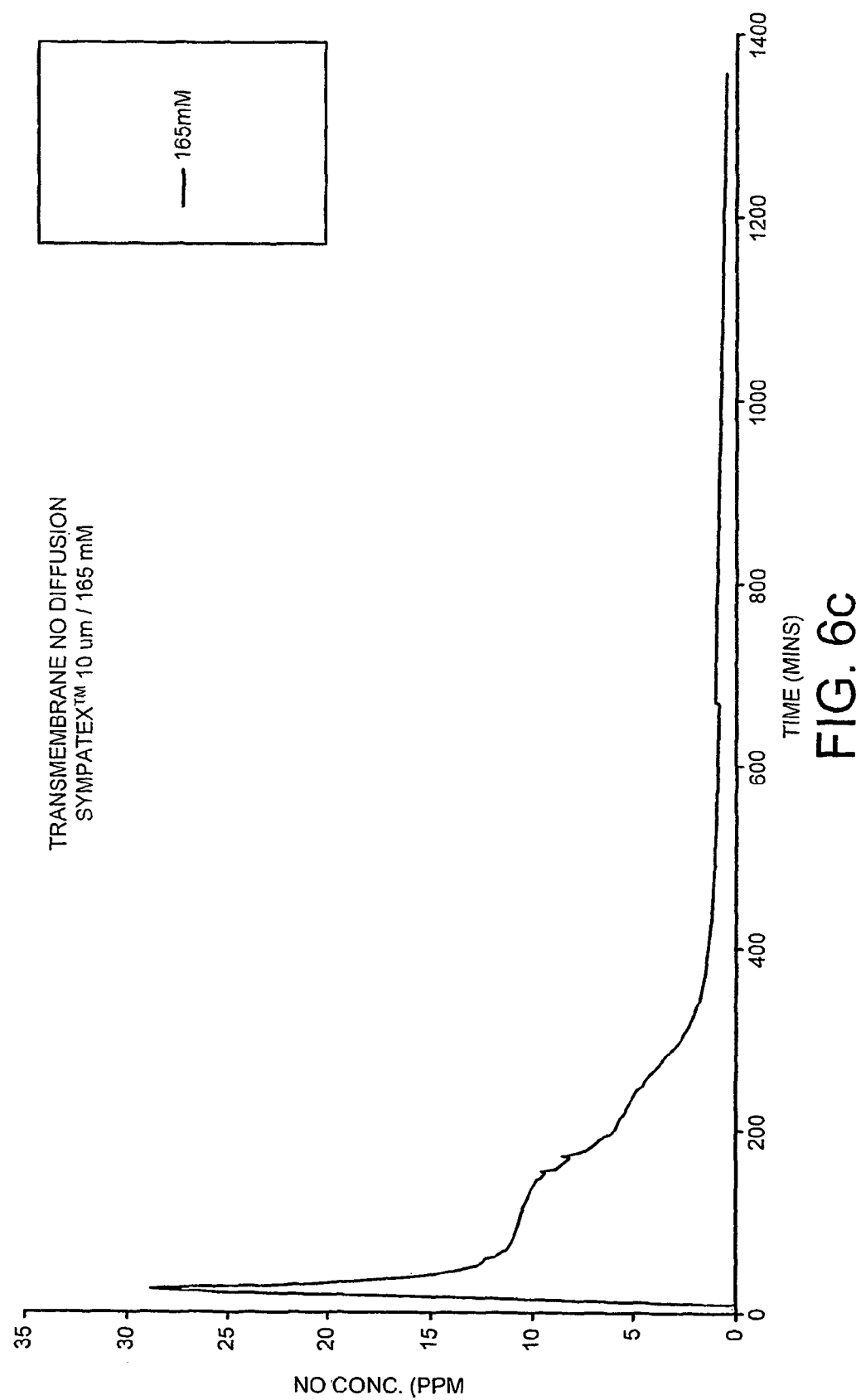

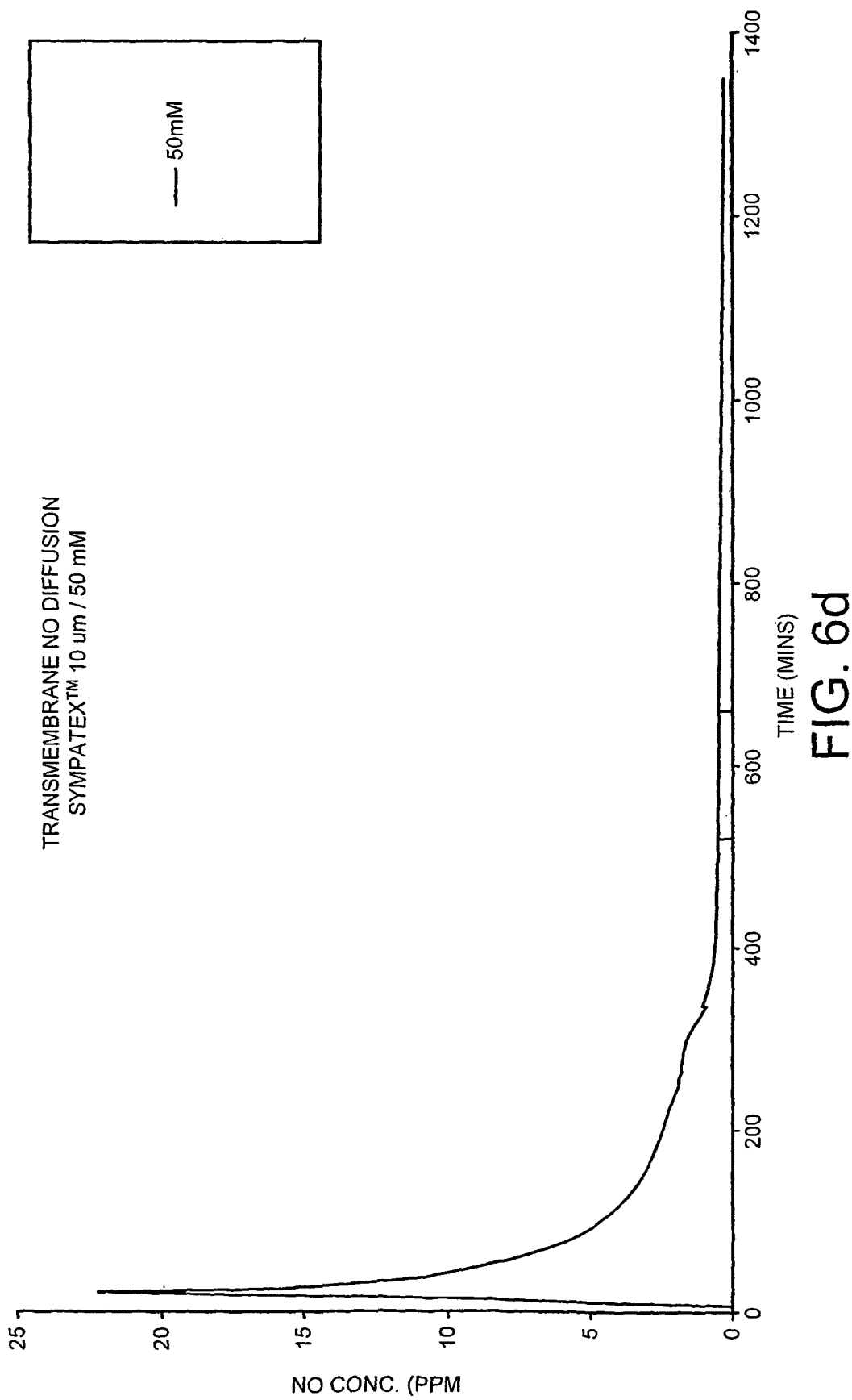

Placebo Treatment
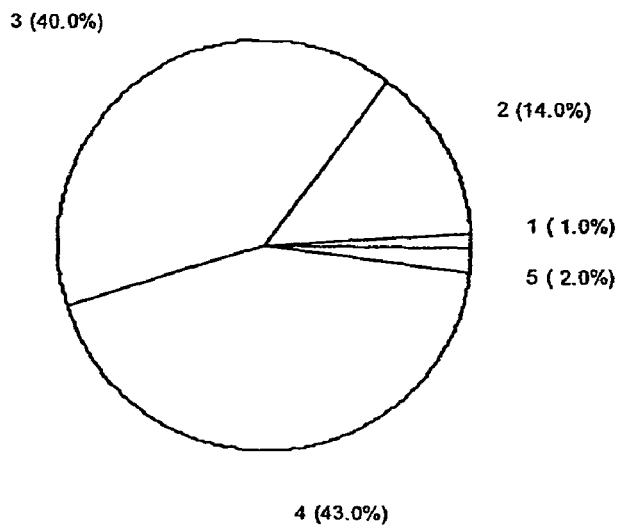
Active Treatment
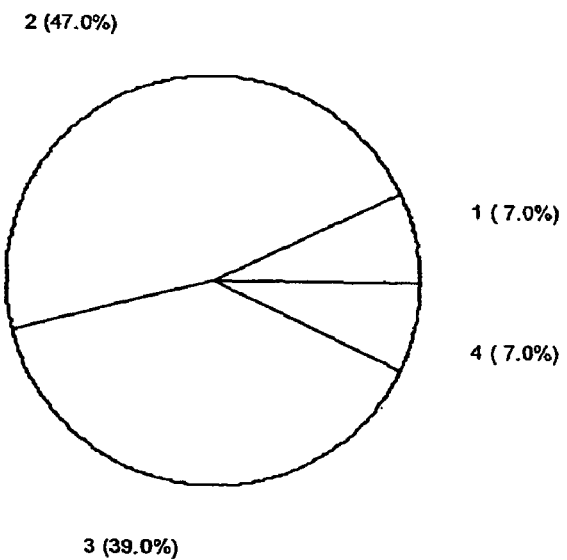
FIG. 8

8,128,964 B2

TRANSDERMAL PHARMACEUTICAL DELIVERY COMPOSITION

BACKGROUND OF THE INVENTION

The present invention relates to a new composition for transdermal delivery of topically applied pharmaceutical preparations. The system comprises the use of the pharmaceutical agent and acidified nitrite contained within a delivery system to allow passage of both the specific pharmaceutical agent and nitric oxide to the skin.

The penetration of substances through the skin is important from both toxicological and therapeutic viewpoints. Passive delivery of most compounds across different epithelia is limited due to the excellent barrier properties afforded by these epithelia. The stratum corneum is the principal barrier to penetration of most chemicals. Conventional topical delivery systems are therefore restricted to either substances for local effects or to highly potent, small, lipophilic substances for systemic effects. It is also difficult to deliver ionic and high-molecular-weight drugs in therapeutically sufficient amounts by conventional systems.

By way of example, many medical and surgical procedures require topical anaesthesia. The use of local anesthetics requires an agent possessing the following general properties. It should not be irritating to the tissue to which it is applied, nor should it cause any permanent damage to nerve structure. Its systemic toxicity should be low because it is eventually absorbed from its site of administration. It is usually important that the time required for the onset of anaesthesia should be as short as possible. Furthermore, the action must last long enough to allow time for the contemplated medical or surgical intervention, yet not so long as to entail an extended period of recovery (J. Murdoch Ritchie & N. M. Greene *Local Anaesthetics in Goodman & Gilman's: The Pharmacological Basis of Therapeutics*, pages 311-331, McGraw-Hill Inc, (1992)).

Local anesthetics are rapidly absorbed into the circulation following topical administration to mucous membranes or denuded skin. It is extremely useful in achieving loss of sensation in a subject without the loss of consciousness, or the impairment of central control of vital functions. Typical uses, include minor invasive procedures such as venepuncture, e.g. for the collection of blood for diagnostic purposes from a patient, for the administration of therapeutic agents, whole blood or blood plasma to a patient, or prior to the administration of a general anaesthetic to a patient. However, it is a common feature among patients that the pain of injection can cause discomfort and in certain cases a patient, in particular juvenile subjects, can experience acute anxiety or panic brought on by the sight of a needle or of the injection itself. Such panic attacks can be characterised by fainting, vomiting or other related symptoms. Whether the adverse reaction is pain or a panic attack, the problem leads to poor patient compliance with advisable medical procedures. There exists a need therefore for improved local anaesthetic compositions that can overcome these problems.

Intact, healthy human skin presents an excellent natural barrier to the external environment and restricts the passive diffusion of pharmaceuticals. Local anaesthetics do not readily penetrate intact skin (McCafferty et al *Br J Anaesth* 60, pages 64-69 (1988)).

The insertion of a needle through the skin, for procedures such as phlebotomy or vaccination, is painful and may induce great fear and anxiety especially in children and the elderly. Painful experiences lead to reduced compliance, with heightened anticipatory anxiety and fear. The introduction of topically-applied cutaneous anaesthetic preparations such as EMLA™ (Eutectic Mixture of Local Anaesthetics) cream [Astra Pharmaceuticals Ltd.] (Arts et al *Pediatrics* 93, pages 797-801 (1994)) and more recently Ametop Gel™ [Smith & Nephew Healthcare Ltd.] (Freeman et al *Paediatr Anaesth* 3, pages 129-138 (1993)), represented a definite advance in clinical practice and are contributing to breaking the cycle of "needle phobia".

Studies of the effects of these preparations have produced variable results (Molodecka et al *Br J Anaesth* 72, pages 174-176 (1994); Lawson et al *Br J Anaesth* 75, pages 282-285 (1995)). However, relatively slow onset times (EMLA™ 60-90 minutes; Ametop Gel™ 30-45 minutes) remain a deterrent to widespread clinical and patient acceptance with the need to organise clinic, ward and operating theatre routines accordingly. These methods are of no benefit in acute situations. Additionally, even following the manufacturer's recommendations for dosage and administration, potential exists for improvement in the degree of anaesthesia afforded by these treatments.

A percutaneous local anaesthetic with a more rapid onset time and increased potency would be helpful in organisational terms for emergency cases, community medicine and for an increasing number of paediatric medical and surgical day cases. Shortening of the period of anticipatory anxiety while achieving the maximal desensitising of the skin would clearly be clinically advantageous.

Nitric oxide [NO] is a potent vasodilator synthesised and released by vascular endothelial cells and plays an important role in regulating vascular local resistance and blood flow (Palmer et al *Nature* 327, pages 524-6 (1987)). In mammalian cells, NO is produced along with L-citrulline by the enzymatic oxidation of L-arginine. Nitric oxide is also involved in the inhibition of both platelet and leukocyte aggregation and adhesion, the inhibition of cell proliferation, the scavenging of superoxide radicals and the modulation of endothelial layer permeability. Nitric oxide also has been shown to possess anti-microbial properties, reviewed by F. C. Fang (1997) (*J. Clin. Invest.* 99 (12) 2818-2825 (1997)).

A potential therapeutic utility of the anti-microbial properties of NO is described in WO 95/22335. A pharmaceutical composition comprising nitrite in an inert carrier cream or ointment and salicylic acid was used to show killing of cultures containing *E. coli* and *C. albicans*. This activity was further tested against patients with fungal infection of the feet ("Athlete's Foot" or *Tidea pedis*) and showed that the condition was amenable to treatment with the acidified nitrite composition. However, the composition of nitrite and organic acid caused erythema (redness) of the skin.

In addition to internal cell-mediated production, NO is also continually released externally from the surface of the skin by a mechanism, which appears to be independent of NO synthase enzyme. Nitrate excreted in sweat is reduced to nitrite by an unknown mechanism, which may involve nitrite reductase enzymes, which are expressed by skin commensal bacteria. Alternatively mammalian nitrite reductase enzymes may be present in the skin which could reduce nitrite rapidly to NO on the skin surface (Weller et al *J Invest Dermatol* 107, pages 327-331 (1996)).

The production of NO from nitrite is believed to be through the following mechanism:

Topical application of a sodium nitrite/ascorbic acid NO-generating system causes significant increases in skin blood flow in patients with Raynaud's disease and in normal healthy subjects without causing local irritation (Tucker et al *Lancet* 354(9191):1670-5 (1999); Harwick et al *Clinical Science* 100, pages 395-400 (2001)). The reaction can be terminated within a few seconds by gentle wiping of the skin with a tissue.

SUMMARY OF THE INVENTION

It has now been found that an improved delivery system for pharmaceutically active agents by topical application to the skin can be prepared from a suitable drug and a source of nitrite ions in an inert carrier cream or ointment when mixed with an organic acid such as ascorbic acid. The source of nitrite ions and the organic acid react to produce oxides of nitrogen to cause sustained vasodilation of the microcirculatory blood vessels, without significant inflammation. This new use for acidified compositions containing nitrite is a departure from the previously known uses of the composition as an anti-microbial agent. The side-effects of erythema associated with the treatment of fungal infections of the foot had been considered to suggest that the composition should not be used on broken skin or away from sites of infection needing immediate, short term therapeutic treatment. Additionally, the skin on the foot is significantly thicker and tougher than elsewhere on the mammalian body and so can endure more prolonged erythema than other thinner areas of skin elsewhere. Furthermore, there is a widespread and generally accepted medical prejudice against inserting ointments or gels into open wounds or onto broken skin. Such practice is advised against because of the risk of actually causing infection or blood poisoning. The administration of a pharmaceutical or pharmaceuticals using this system has advantages over previous modes of administration.

This system overcomes the limitations associated with conventional transdermal pharmaceutical application and is feasible for ionisable, hydrophilic and higher molecular weight compounds. The pharmaceuticals enter the skin through intracellular spaces and specialised tissues such as eccrine and apocrine sweat ducts and hair follicles with sebaceous glands.

The system depends upon several variables in addition to factors, which affect the skin uptake of drugs during passive diffusion. These include vehicle pH, ionic strength, transport number of ions and water, drug conductivity, solute concentration and skin impedance.

With reference to systemically active compounds, transdermal delivery has several advantages, particularly avoidance of gastrointestinal incomparability and hepatic "first-pass" effect. Additionally, the nitric oxide induced vasodilation of the skin microcirculation significantly enhances percutaneous absorption of the pharmaceutical agent in to the systemic circulation.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures.

FIG. 3 shows nitric oxide diffusion through a selection of membranes where the vertical axis shows nitric oxide concentration and the horizontal axis is the time in minutes. FIG. 3a shows the results using Saranwrap™ (SW-01) and FIG. 3b shows the results using Clingfilm (CF-02).

FIG. 5 shows the diffusion effect of the treatment through a membrane on the forearm skin microcirculatory blood flow in a healthy subject. The vertical axis is blood flow, laser Doppler fluximetry (LDF) relating to microcirculatory flux and the horizontal axis is the time in minutes.

FIGS. 6(a)-(i) show the transmembrane diffusion for sodium nitrite and ascorbic acid in 0.8% agar gel, using 1% sodium chloride as an intermediate at final concentrations of 500 mM, 250 mM, 165 mM, 50 mM, 25 mM, 5 mM, 2.5 mM and 0.5 mM. A control of nitrite and 0.8% agar gel using 1% sodium chloride as an intermediate was also used. The figure illustrates nitric oxide diffusion through Sympatex™ 10 μm (Akzo Nobel) membrane where the vertical axis shows the nitric oxide concentration in parts per million (PPM) and the horizontal axis shows the time in minutes. In FIGS. 6(a) and 6(b) the initial peaks are artificially flattened due to the full scale deflection of the detection device.

FIG. 8 shows results of pain levels experienced by subjects using Verbal Rating Score (VRS); values are categories (percentage); n=100; $P<0.0001$ [1] no pain; [2] minimal sensation; [3] mild pain; [4] moderate pain; [5] severe pain (including withdrawal of hand).

DETAILED DESCRIPTION OF THE PREFERRED EMBODIMENTS OF THE INVENTION

Figure 1:
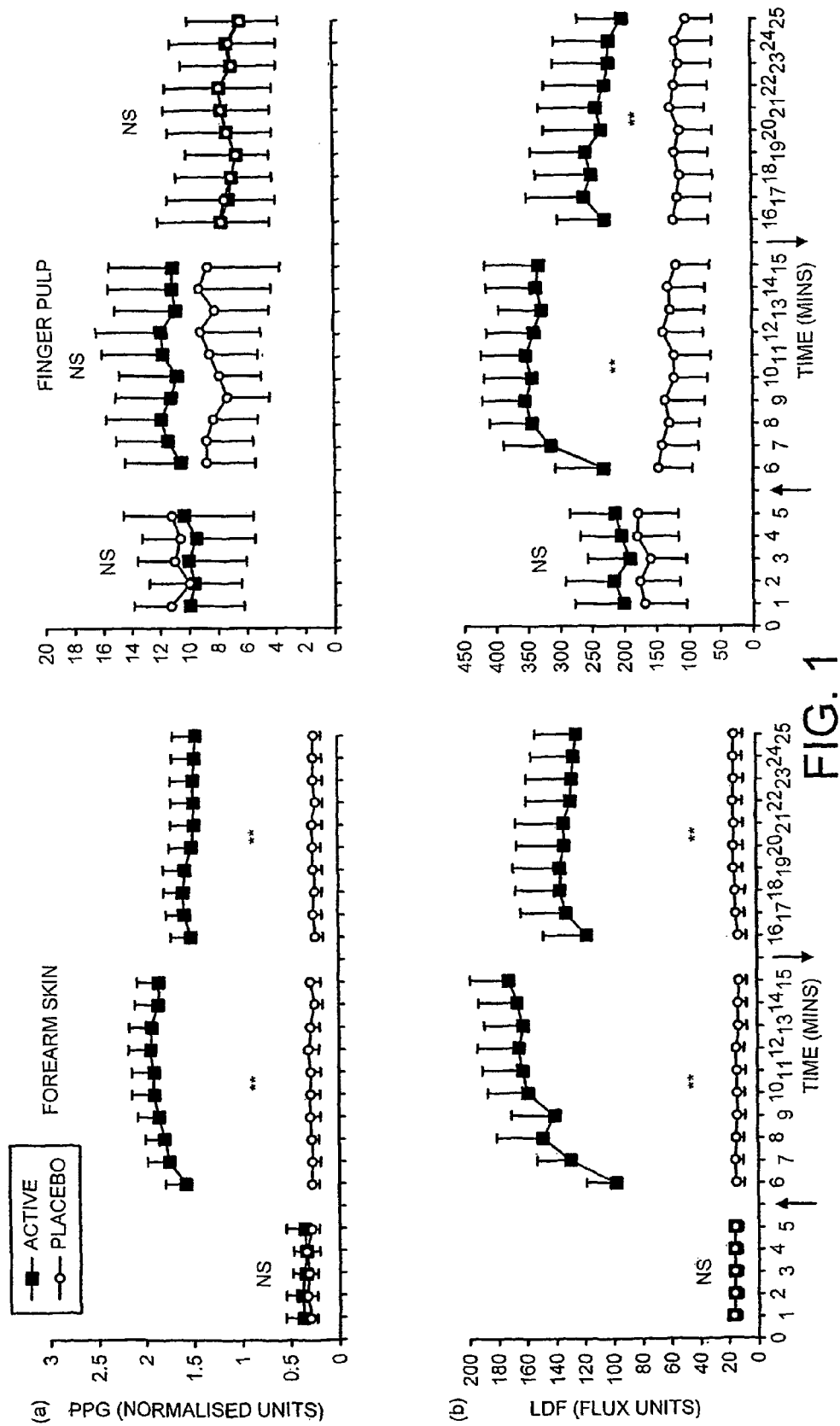
FIG. 1 shows the effect of direction application and subsequent removal of the treatment on the microcirculatory blood flow in forearm skin and finger pulps of healthy subjects. The vertical axes are blood flow, photoplethysmography (PPG) relating to microcirculatory volume and laser Doppler fluximetry (LDF) which relates relating to microcirculatory flux (red blood cell count×velocity). The horizontal axis is the time in minutes; NS=not significant; points shown represent the mean value; error bars are 95% confidence; *=$p<0.05$; =$p<0.01$; *=$p<0.001$; ↑=application of gel; and ↓=removal of gel.

According to a preferred embodiment of the invention there is provided a composition comprising a pharmaceutically active agent, a pharmacologically acceptable acidifying agent, a pharmacologically acceptable source of nitrite ions or a nitrite precursor therefor.

The pharmaceutically active agent may comprise any suitable drug or combination of drugs to treat a disease in a patient. The agent may be immediately active in the form administered or may become active in the body of the patient following administration, such as for example through hydrolysis or by the action of an endogenous enzyme. In principle, any pharmaceutically active substance can be administered using this delivery system.

Therapeutically, the novel system facilitates the delivery of a wide number of systemically active substances. Active substances include, but are not limited to, antibiotics, hormones, proteins, peptides, proteogylcans, nucleotides, oligonucleotides (such as DNA, RNA, etc.), vitamins, minerals, growth factors, non-steroidal anti-inflammatory drugs (NSAIDs). In a preferred embodiment, the delivery system of the present invention can be used to deliver anaesthetic, analgesic, hormone, immunosuppressant or steroid formulations. Other pharmaceutical agents include, but are not limited to, analgesic agents such as ibuprofen, indomethacin, diclofenac, acetylsalicylic acid, paracetamol, propranolol, metoprolol, oxycodone, thyroid releasing hormone, sex hormones such as oestrogen, progesterone and testosterone, insulin, verapamil, vasopressin, hydrocortisone, scopolamine, nitro-glycerine, Isosorbide dinitrate, anti-histamines (such as terfenadine), clonidine and nicotine, immunosuppressant drugs (such as cyclosporin), steroids.

The anaesthetic can be any appropriate anaesthetic for local anaesthesia and can be provided in aqueous or powdered form, for example, amethocaine (tetracaine), lignocaine (lidocaine), xylocaine, bupivacaine, prilocaine, ropivacaine, benzocaine, mepivocaine or cocaine, or a mixture thereof, preferably in the hydrochloride form. The general concentration range is around 1 to 4% w/w, although greater or lesser amounts can be empirically determined by a physician. Suitably preferred concentrations are tetracaine (0.01 to 10% w/w, suitably 1 to 8% w/w, preferably 2% w/w), lidocaine (0.01 to 10% w/w, suitably 1 to 8% w/w, preferably 5% w/w) and cocaine (1 to 4% w/w). Generally accepted safe dosages of such compounds for topical anaesthesia in a healthy 70 kg-adult are 750 mg for lidocaine, 200 mg for cocaine, and 50 mg for tetracaine. Other suitable anaesthetics are within the competence of the medical practitioner and can also be used in the composition of the present invention at the relevant concentrations.

Prior art methods of improving local anaesthesia have suggested the use of low concentrations of vasoconstrictors, such as phenylephrine (0.005%). However, the compositions of the present invention utilise a previously unknown property of an acidified nitrite composition to produce NO, a vasodilator, which accelerates the transfer of anaesthetic into the dermis. The combination of the NO-generating system and anaesthetic will promote patient compliance of venepuncture and blood-letting techniques by reducing the pain experienced during the procedure.

The choice of pharmaceutically active agent may be determined by its suitability for the treatment regimen of the disease or medical condition concerned and reference can be made to standard reference works such as *Martindale*, the *Merck Index*, Goodman & Gilman's "*The pharmacological basis of therapeutics*", eighth edition (1992), McGraw Hill.

The pharmacologically acceptable acidifying agent is adapted to reduce the pH at the site of application and can include any suitable organic acid. For example, the organic acid can be a $(C_1-C_6)$ alkyl carboxylic acid, a $(C_6-C_{10})$ aryl $(C_1-C_6)$ carboxylic acid.

As used herein, the term "$(C_1-C_6)$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl. The term "$(C_6-C_{10})$ aryl" includes phenyl and naphthyl.

According to *Martindale The Extra Pharmacopoeia*, $28^{th}$ edition (1982), pharmaceutically acceptable acidifying agents can include: dilute hydrochloric acid, betaine hydrochloride, acetic acid, citric acid, citric acid monohydrate, fumaric acid, lactic acid, maleic acid, malic acid, tartaric acid Other acceptable acidifying agents, include but are not limited to, hexose or pentose sugar molecules substituted with a $(C_1-C_6)$ carboxyl group, or furanolactone or pyranolactone molecules substituted with a $(C_1-C_6)$ carboxyl group.

Preferred acidifying agents, include, but are not limited to, ascorbic acid (vitamin C), salicylic acid, acetyl salicylic acid, a $(C_1-C_6)$ alkyl carboxylic acid, for example ethanoic acid (acetic acid), citric acid, or a salt, or a derivative thereof in a concentration up to 20% w/w, suitably 0.25 to 10% w/w, preferably 4 to 6% w/w. A particularly preferred concentration is 4% or 5% w/w. The preferred pH range is from pH2 to pH7, preferably pH4. Other acidifying agents include but are not limited to, ammonium or aluminium salts, $(C_6-C_{10})$ aryl compounds such as phenol, benzoic acid or derivatives thereof. Inorganic acids such as hydrochloric acid may be used if sufficient dilute and/or appropriately buffered. The acidifying agent may be present as a dissolved salt or in a liquid form.

The pharmacologically acceptable source of nitrite ions may an alkali metal nitrite or an alkaline earth metal nitrite. For example, $LiNO_2$, $NaNO_2$, $KNO_2$, $RbNO_2$, $(CsNO_2$, $FrNO_2$, $Be(NO_2)_2$, $Mg(NO_2)_2$, $Ca(NO_2)_2$, $Sr(NO_2)_2$, $Ba(NO_2)_2$, or $Ra(NO_2)_2$. Alternatively, a nitrite precursor may be used as the source of the nitrite ions in the composition, such as for example a dilute solution of nitrous acid. Other sources of nitrite ions are nitrate ions derived from alkali metal or alkaline earth metal salts capable of enzymic conversion to nitrite. For example, $LiNO_3$, $NaNO_3$, $KNO_3$, $RbNO_3$, $CsNO_3$, $FrNO_3$, $Be(NO_3)_2$, $Mg(NO_3)_2$, $Ca(NO_3)_2$, $Sr(NO_3)_2$, $Ba(NO_3)_2$, or $Ra(NO_3)_2$. The concentration of the nitrate ion source may be up to 20% w/w. suitably 0.25 to 10%, preferably 4 to 6%. A particularly preferred concentration is 4% or 5% w/w.

Suitably, the final nitrite ion concentration present in the composition is up to 20% w/w, generally in the range of from 0.25% to 15% w/w, suitably 2% to 10% w/w, preferably 4 to 6% w/w. A particularly preferred nitrite ion concentration is 4% or 5% w/w.

In the preparation of an agent according to this embodiment of the invention, the pharmaceutically active agent, the acidifying agent and the nitrite ions or source therefor are formulated in a pharmacologially acceptable carrier or diluent which may be an inert cream or ointment. In a particular preferred form of the invention, the pharmaceutically active agent, the acidifying agent and the source of nitrite ions or precursor therefor are separately disposed in the said cream or ointment for admixture to release ions at the environment of use.

The pharmaceutical composition may be adapted for administration by any appropriate topical route, including buccal, sublingual or transdermal. Such compositions may be prepared by any method known in the art of pharmacy, for example by admixing the active ingredient with the carrier(s) or excipient(s) under sterile conditions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils. For treatment of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used.

This dosage may be repeated as often as appropriate. If side effects develop the amount and/or frequency of the dosage can be reduced, in accordance with normal clinical practice.

Such compositions may be formulated for human or for veterinary medicine. The present application should be interpreted as applying equally to humans as well as to animals, unless the context clearly implies otherwise.

According to another preferred embodiment of the invention there is provided the use of a composition as defined above in medicine. In another preferred embodiment, there is provided the use of a pharmaceutically active agent, a pharmacologically acceptable acidifying agent, a pharmacologically acceptable source of nitrite ions or a nitrite precursor therefor in the preparation of an agent for the treatment of a disease or a medical condition. The medical condition can include local anaesthesia, immunosuppression, e.g. to prevent transplant rejection. Diseases suitable for treatment using the delivery system of the present invention include, but are not limited to, cardio-vascular diseases, neurological diseases or disease of the central nervous system (e.g. multiple sclerosis, Parkinsons' Disease), epilepsy, psychiatric disorders (e.g. schizophrenia), inflammation (e.g. rheumatoid arthritis, osteoarthritis, asthma, gout), in particular topical inflammation, hypertension, arrhythmia, hyperlipoproteinemias, gastrointestinal disorders (e.g. peptic ulcers), kidney disease, parasite infections (e.g. protozoal infection, helminthiasis, amebiasis, giardiasis, thichomoniasis, leishmaniasis, trypanosomiasis, malaria), microbial infection (e.g. yeast, fungus, bacteria), viral infection, cancer, immunosuppression, blood disorders (blood clots etc.), endocrine (e.g. hormonal) disorders (e.g. thyroid condition, hypoglycaemia), diabetes, dermatological disorders (e.g. psoriasis).

According to an additional embodiment of the invention, there is provided a method for the local anaesthesia of the skin of a patient, comprising the administration of a composition comprising an anaesthetic, a pharmacologically acceptable acidifying agent, a pharmacologically acceptable source of nitrite ions or a nitrite precursor therefor.

According to yet another embodiment of the invention, there is provided a composition comprising a pharmaceutically active agent, a pharmacologically acceptable acidifying agent, a pharmacologically acceptable source of nitrite ions or a nitrite precursor therefor as a combined preparation for simultaneous, separate or sequential use in treatment of a disease or medical condition defined above.

According to a further embodiment of the invention, there is provided a kit comprising a pharmaceutically active agent, a pharmacologically acceptable acidifying agent and a pharmacologically acceptable source of nitrite ions or a nitrite precursor therefor for use as a combined preparation in the treatment of a disease or medical condition defined above.

According to an additional embodiment of the present invention, there is provided a permeable membrane comprising a pharmaceutically active agent, a pharmacologically acceptable acidifying agent and pharmacologically acceptable source of nitrite ions or a nitrite precursor therefor. The membrane may be fully-, or partially-permeable, including semi-permeable, to the passage of nitric oxide. Such membranes can prevent direct contact of the composition with the skin but can permit diffusion of nitric oxides into the skin. This is particularly advantageous in the treatment of areas of broken skin, open wounds, or serious burns. In this way, the integrity of the wound area is preserved. Suitable membranes include, but are not limited to, polymeric materials such as nitrocellulose, cellulose, agarose, polyethylene, polyester (for example, hydrophilic polyester block copolymer), etc. A suitable membrane that can be used in practice is Sympatex™ which is composed of fibres of hydrophilic polyester block copolymer.

Preferred features for all additional and foregoing described embodiments of the invention are as for the first described embodiment mutatis mutandis.

EXAMPLES

The invention will now be described, by way of illustration only with reference to the following examples, which are provided for the purposes of illustration and are not to be construed as being limiting on the invention.

Example 1

Microcirculatory Response to Topical Application of NO-Generating Gel in Healthy Subjects A nitric oxide-generating gel (NO-generating gel) was prepared as follows. Sodium nitrite (Analar™ grade from Sigma, Poole, Dorset, UK) was added to KY Jelly™ (Johnson & Johnson) to make a 5% w/w solution. Ascorbic acid (Sigma) was also added to KY Jelly™ (Johnson & Johnson) to make a 5% w/w solution. Approximately 0.5 ml of each solution was mixed together on the skin of a patient using a sterile swab. When the two solutions are brought into contact, the ensuing reaction leads to the generation of nitric oxide. The reaction may be stopped by cleaning the skin with paper or a swab soaked in ethyl alcohol.

With reference to FIG. 1 the microcirculatory response to topical application of NO-generating gel was measured in 10 healthy subjects. The effect of placebo treatment was measured simultaneously on the contra-lateral limb. The skin microcirculatory volume was measured by infra-red photoplethysmography [PPG] and microcirculatory velocity by laser Doppler fluxmetry [LDF]. All examinations were performed in a quiet, draught-free, temperature and humidity controlled laboratory (24° C.±1° C.; relative humidity 30-40%) in the morning at approximately the same time of day for each subject.

Placebo treatment did not have any effect upon microcirculatory blood flow in either the forearm or the finger of the normal subjects. The vasodilator response to the active treatment reached a plateau phase in all patients within the ten minutes of active gel application. Forearm skin and finger pulp blood flow increased markedly following topical application of a NO-generating gel in the healthy volunteers. When the active gel was applied to the forearm skin all subjects showed a large vasodilator response to active gel treatment in both volume and flux. This increase in blood flow was sustained after removal of the active gel. The active gel had no significant effect on finger microcirculatory volume (PPG) (FIG. 1: Finger pulp), however microcirculatory flux increased significantly ($p<0.01$) and remained so after removal ($p<0.01$; FIG. 1: Finger pulp).

Example 2

Figure 2:
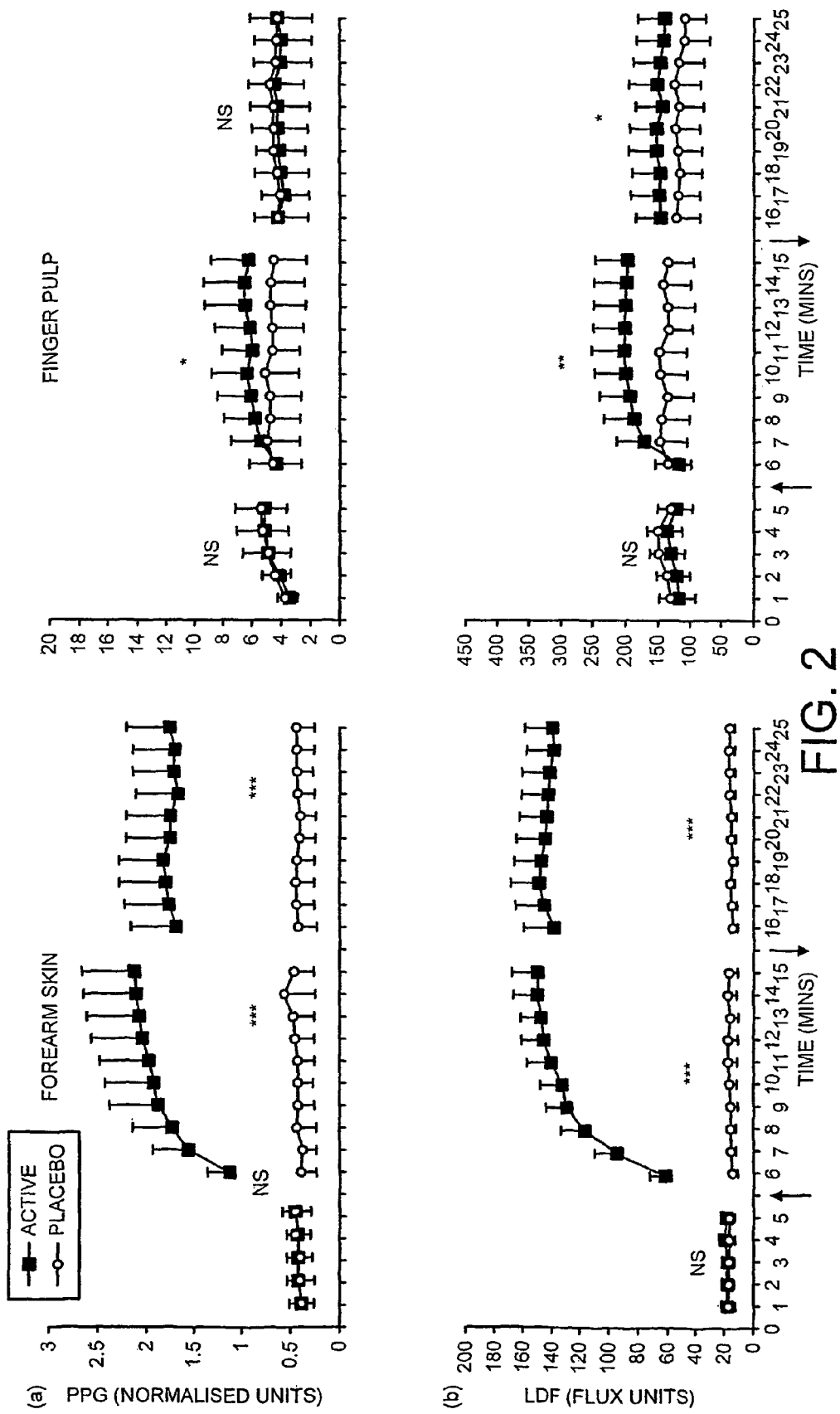
FIG. 2 shows the effect of direct application and subsequent removal of the treatment on the microcirculatory blood flow in forearm skin and finger pulps of subjects with severe Raynaud's phenomenon. The vertical axes are blood flow, photoplethysmography (PPG) relating to microcirculatory volume and laser Doppler fluximetry (LDF) which relates to microcirculatory flux. The horizontal axis is the time in minutes.

Microcirculatory Response to Topical Application of NO-Generating Gel in Patients With Severe Primary Vasospasm FIG. 2 shows the microcirculatory response to topical application of NO-generating gel was measured in 20 patients with severe primary vasospasm. The effect of the placebo treatment was measured simultaneously on the contra-lateral limb. Conditions were the same as those used for the application of the treatment on healthy subjects in FIG. 1. The skin microcirculatory volume was measured by infra-red photoplethysmography [PPG] and microcirculatory velocity by laser Doppler fluxmetry [LDF].

Placebo treatment did not have any effect upon microcirculatory blood flow in either the forearm or the finger of any patients. The vasodilator response to the active treatment reached a plateau phase in all patients within ten minutes of the application of active gel. When the gel was applied to the forearm skin all patients showed a large vasodilator response to active gel treatment in both volume and flux. This increase in blood flow was sustained after removal of the active gel in both groups (FIG. 2: Forearm and finger pulp). The active gel to the finger pulp caused a significant increase in microcirculatory volume ($p<0.05$) which returned rapidly to the resting level on removal of the gel. Active gel also significantly increased finger microcirculatory flux ($p<0.01$) which achieved normal values. This increase was sustained, although reduced, after removal of the gel ($p<0.05$).

Example 3

Generation of Nitric Oxide Derived through a Membrane

Figure 3B:
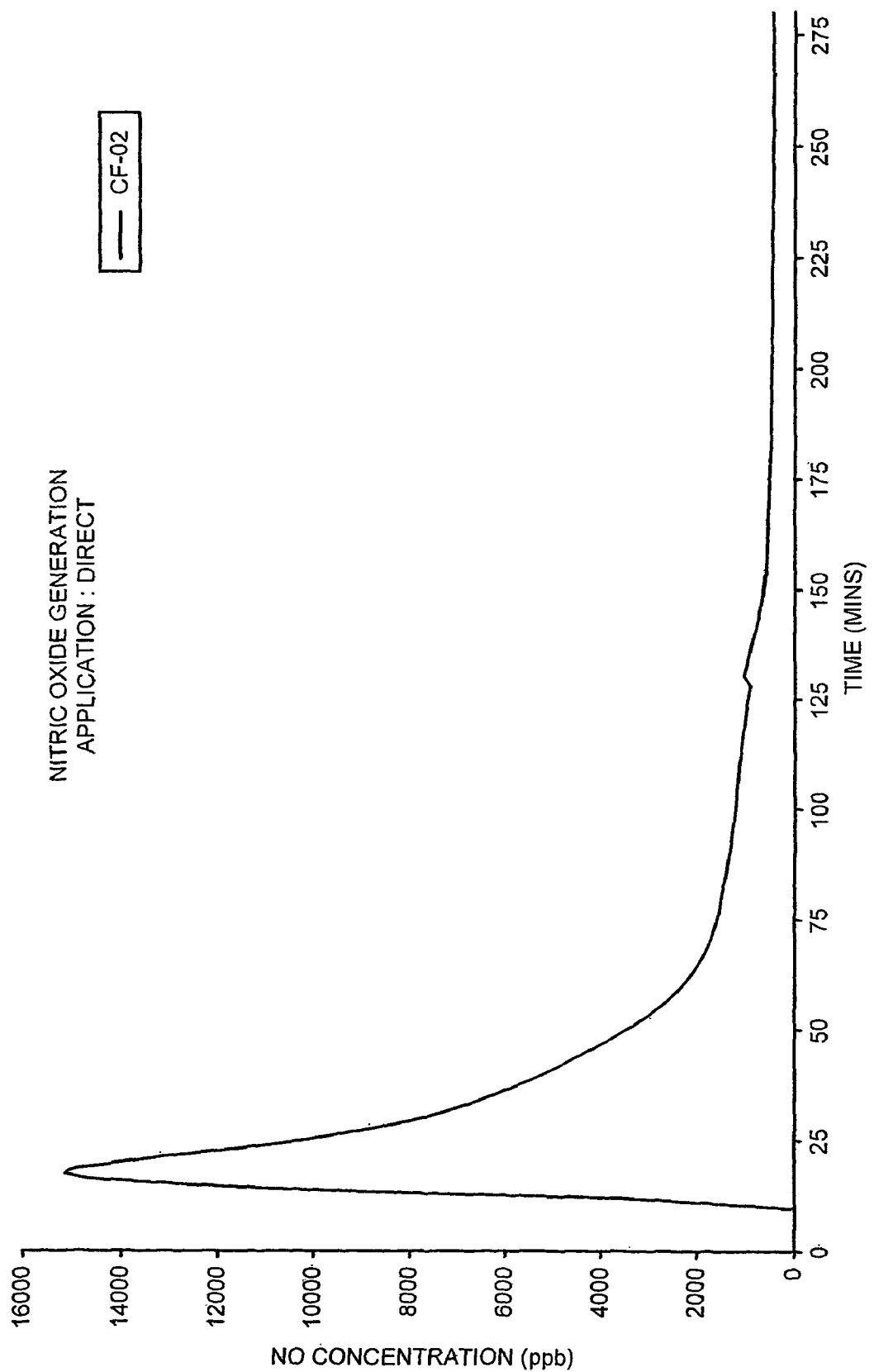

FIG. 3 shows the generation of nitric oxide derived from the reaction previously detailed through a membrane. Nitric oxide concentrations were measured by a nitric oxide sensitive meter: Model 42C Chemiluminescence $NO-NO_2-NO_x$ analyser (Thermo Environmental Instruments Inc., MA USA) connected to a data acquisition system and IBM computer. Measurements were made continually and readings were taken every 10 seconds for 275 minutes. Material 1 was domestic Clingfilm, Material 2 was Saranwrap™ (Sigma) and Material 3 was (Sympatex™ Akzo Nobel).

Example 4

Figure 4:
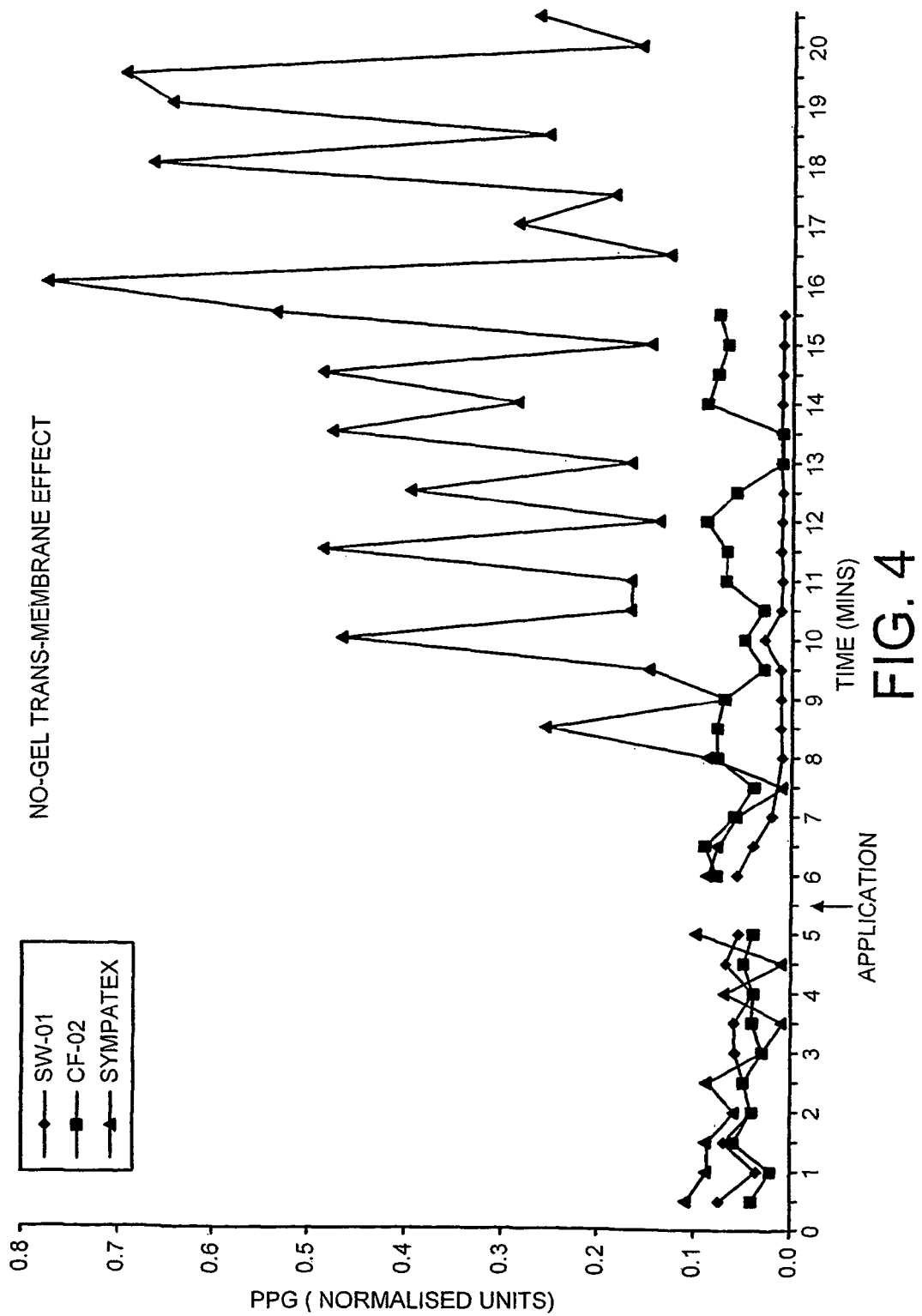
FIG. 4 shows the diffusion effect of the treatment through a membrane on the forearm skin microcirculatory blood flow in a healthy subject. The vertical axis is blood flow, photoplethysmography (PPG) relating to microcirculatory volume and the horizontal axis is the time in minutes.
Figure 6A:
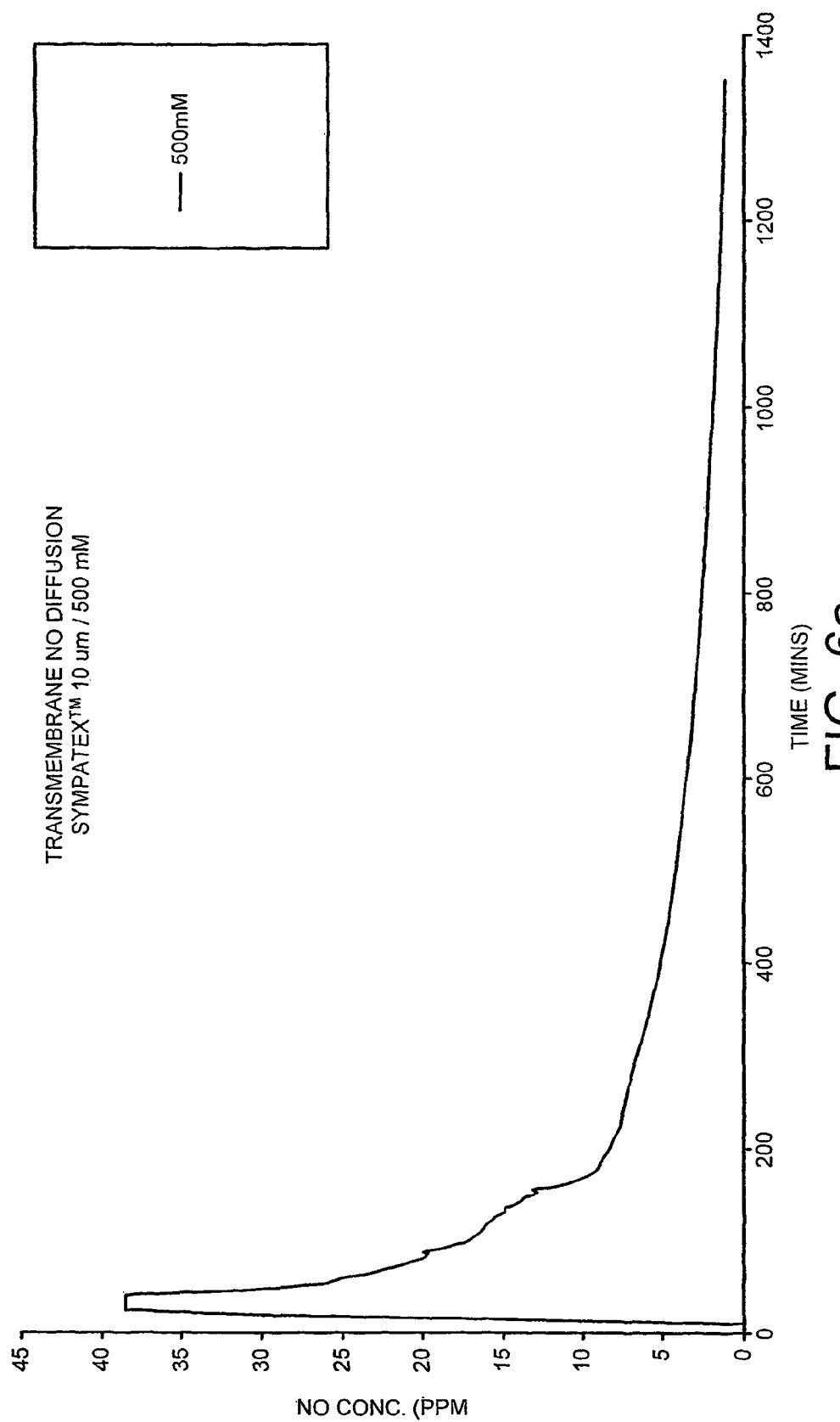
Figure 6B:
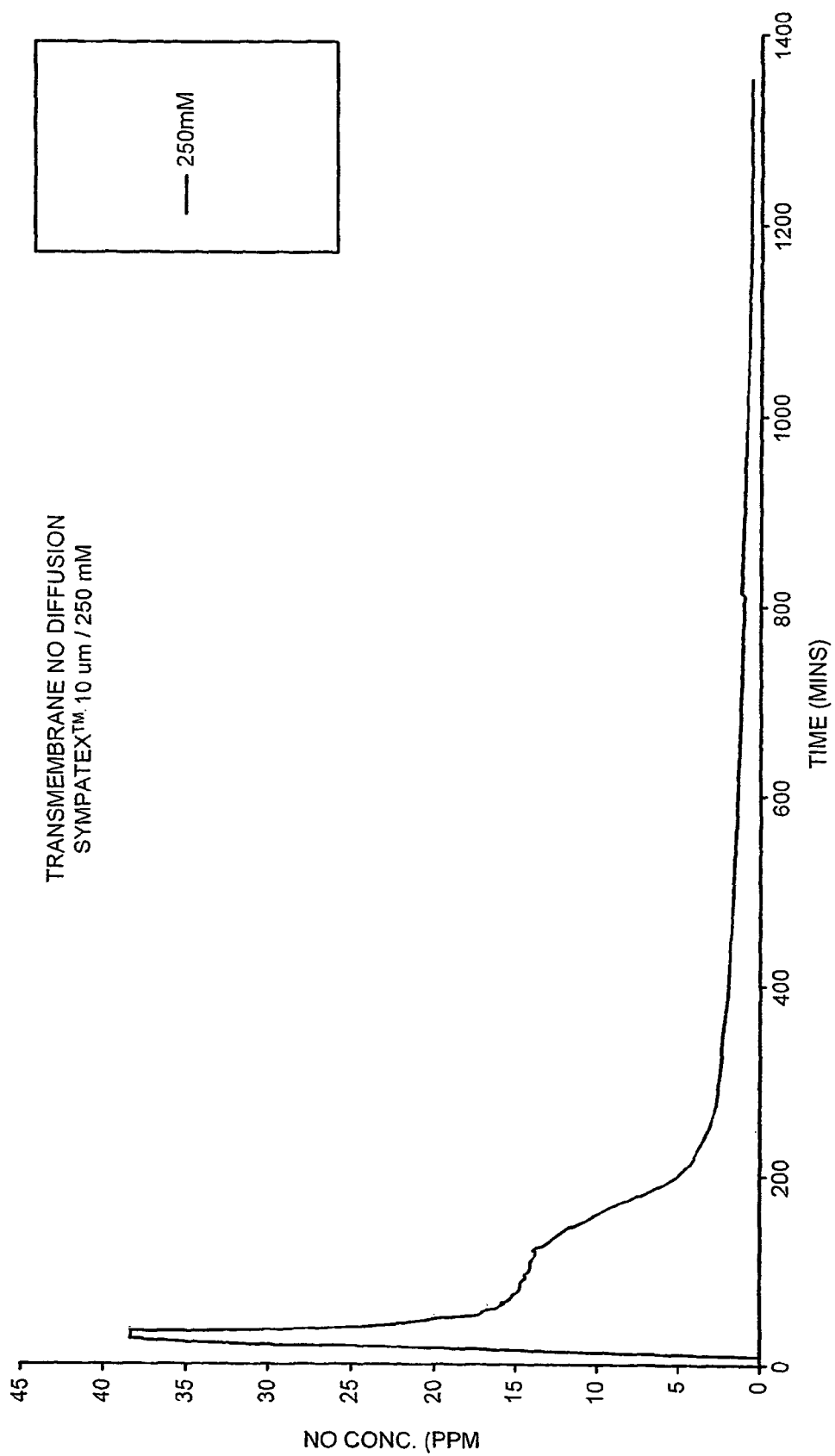
Figure 6E:
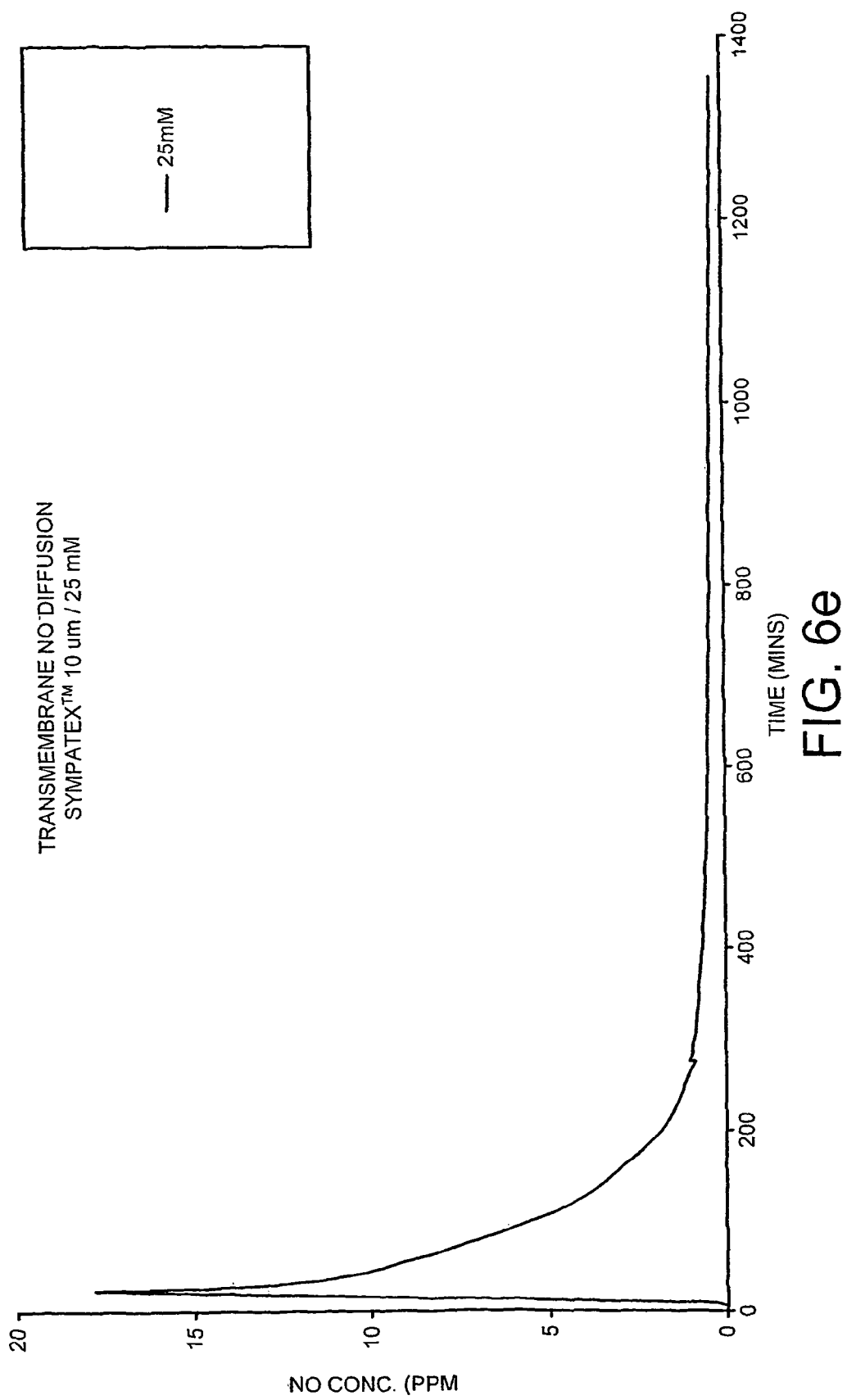
Figure 6F:
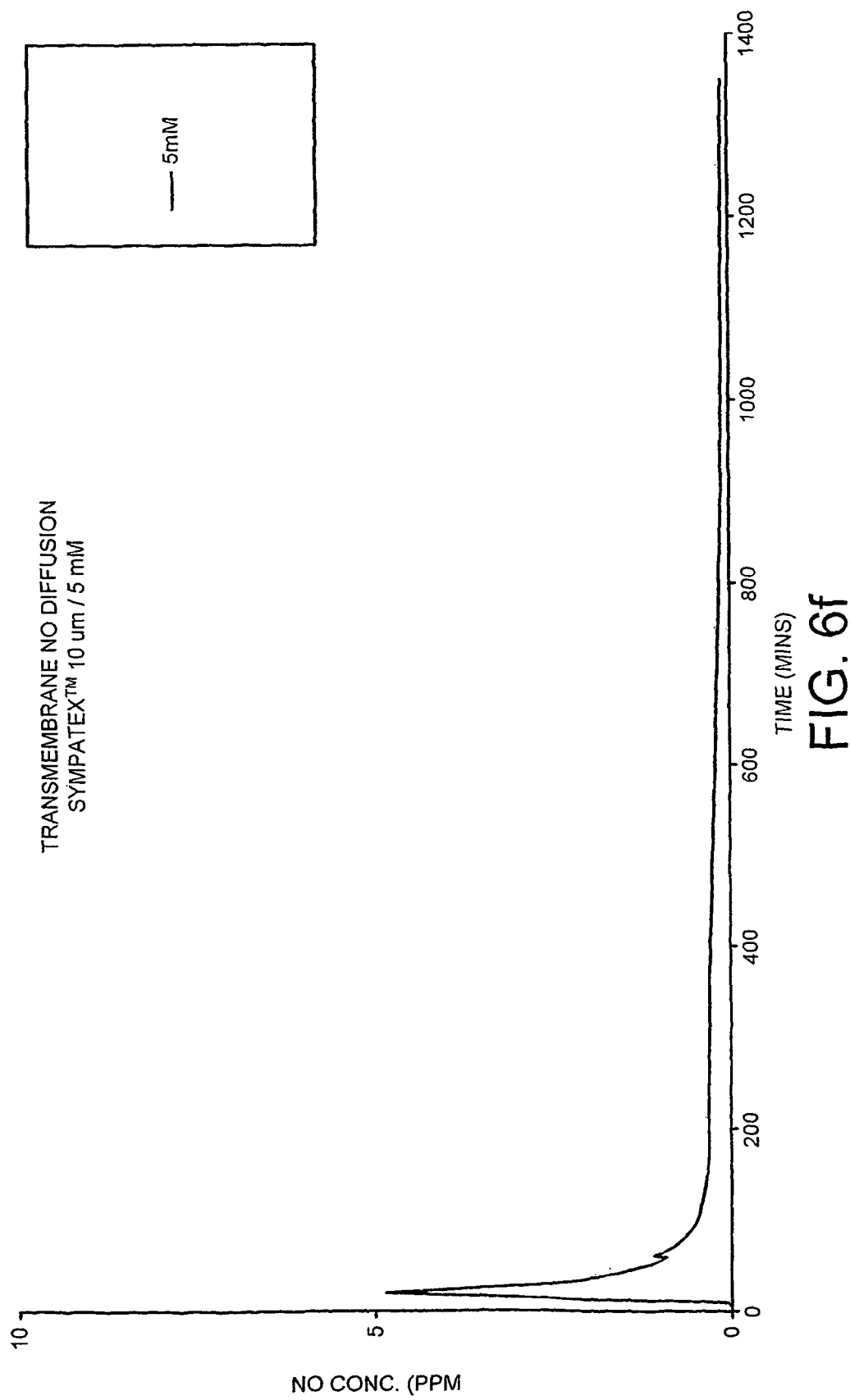
Figure 6G:
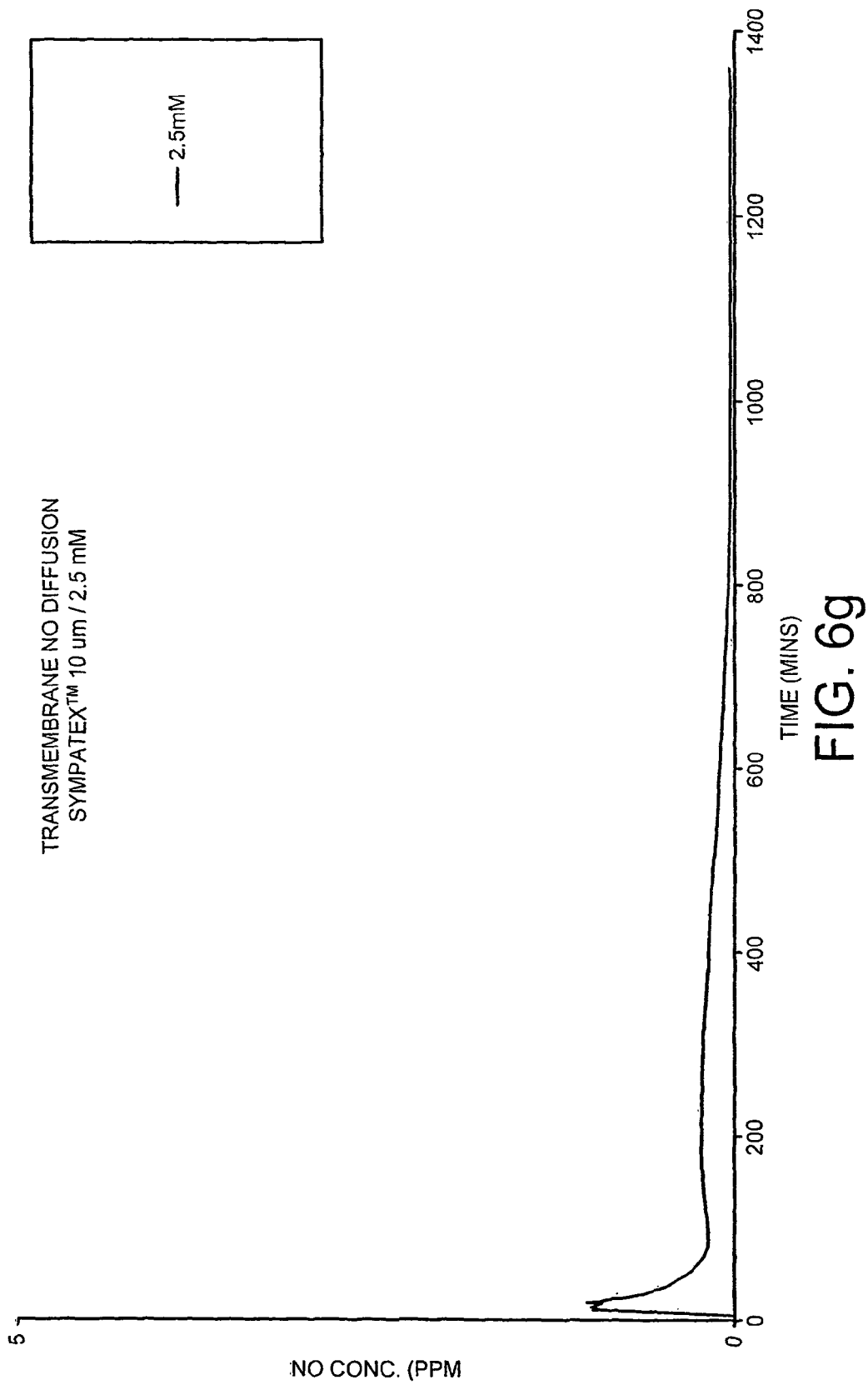
Figure 6H:
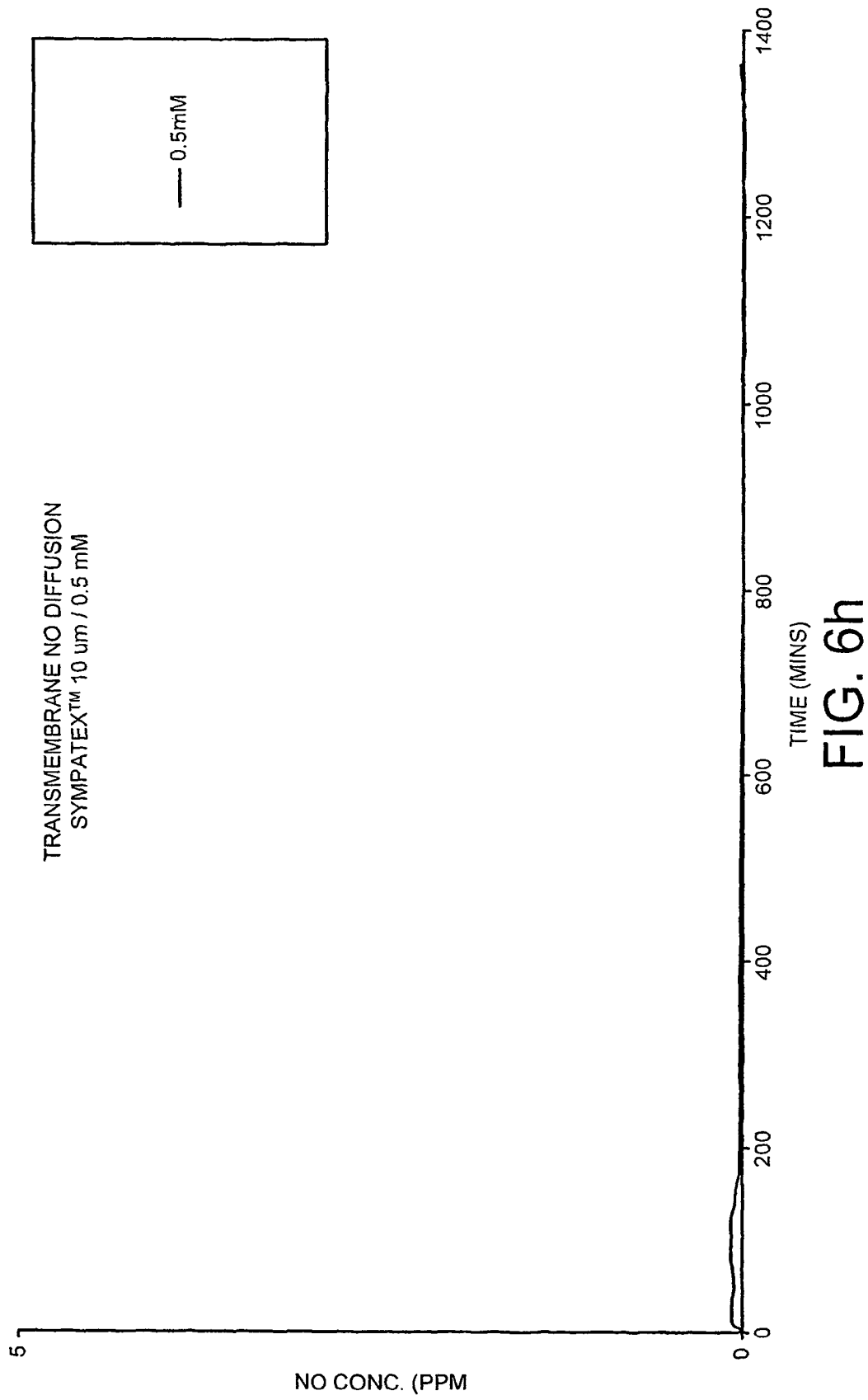
Figure 6I:
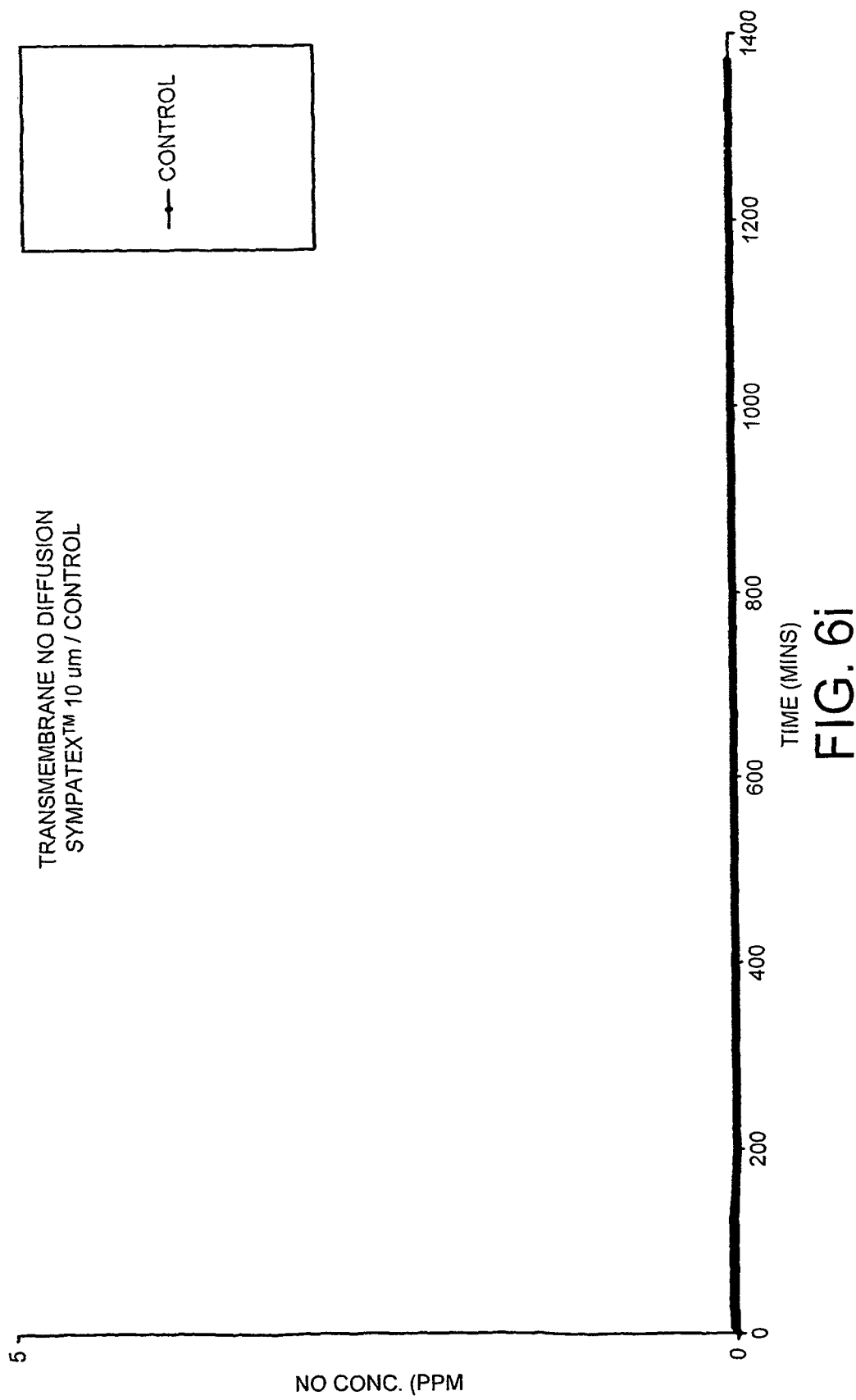

Microcirculatory Response of the Application of NO-Generating Gel to Three Differing Membrane Materials FIG. 4 shows the microcirculatory response of the application of NO-generating gel to three differing membranes which were then applied to the forearm skin of a healthy subject. Conditions were the same as those used for the application of the treatment upon healthy subjects in FIG. 1. The skin microcirculatory volume was measured by infra-red photoplethysmography [PPG]. Material 1 was domestic Clingfilm, Material 2 was Saranwrap™ (Sigma) and Material 3 was (Sympatex™, Akzo Nobel).

The increase in microcirculatory blood volume is a reflection of the diffusion of nitric oxide through the membrane towards the skin; The transfer of nitric oxide through the membrane is a reflection of the physical characteristics of the material and is highly variable. Material number 3 (Sympatex™, Akzo Nobel) had a superior diffusion profile.

Example 5

Microcirculatory Response of the Application of NO-Generating Gel to Three Differing Membrane Materials FIG. 5 shows the microcirculatory response of the application of NO-generating gel to three differing membranes which were then applied to the forearm skin of a healthy subject. Conditions were the same as those used for the application of the treatment on healthy subjects in FIG. 1. The skin microcirculatory velocity was measured by laser Doppler fluxmetry [LDF].

The increase in microcirculatory velocity is a reflection of the diffusion of nitric oxide through the membrane towards the skin. The transfer the nitric oxide through the membrane is a reflection of the physical characteristics of the material and is highly variable. Material number 3 (Sympatex™, Akzo Nobel) had a superior diffusion profile.

Example 6

Comparison of Nitric Oxide Generation through a Membrane

FIG. 6 shows the generation of nitric oxide derived from the reaction described above through a 10 μm Sympatex™ membrane. Nitric oxide concentrations were measured by a nitric oxide sensitive meter: Model 42C chemiluminescence $NO-NO_2-NO_x$ analyser (Thermo Environmental Instrumental Inc., MA, USA) connected to a data acquisition system and an IBM computer. Measurements were made continually and readings were taken every 10 seconds for 1350 minutes.

The results shown in FIG. 6 illustrate that the transmembrane diffusion coefficient is closely related to the production of nitric oxide, which is a direct product of the concentration of both the source of the nitrite ions and the acidifying agent.

Furthermore, the results demonstrate that a basal production of nitric oxide is sustained for a significant period of time after mixing the reagents.

Example 7

Microcirculatory Response of the Application of NO-Generating Gel

Figure 7:
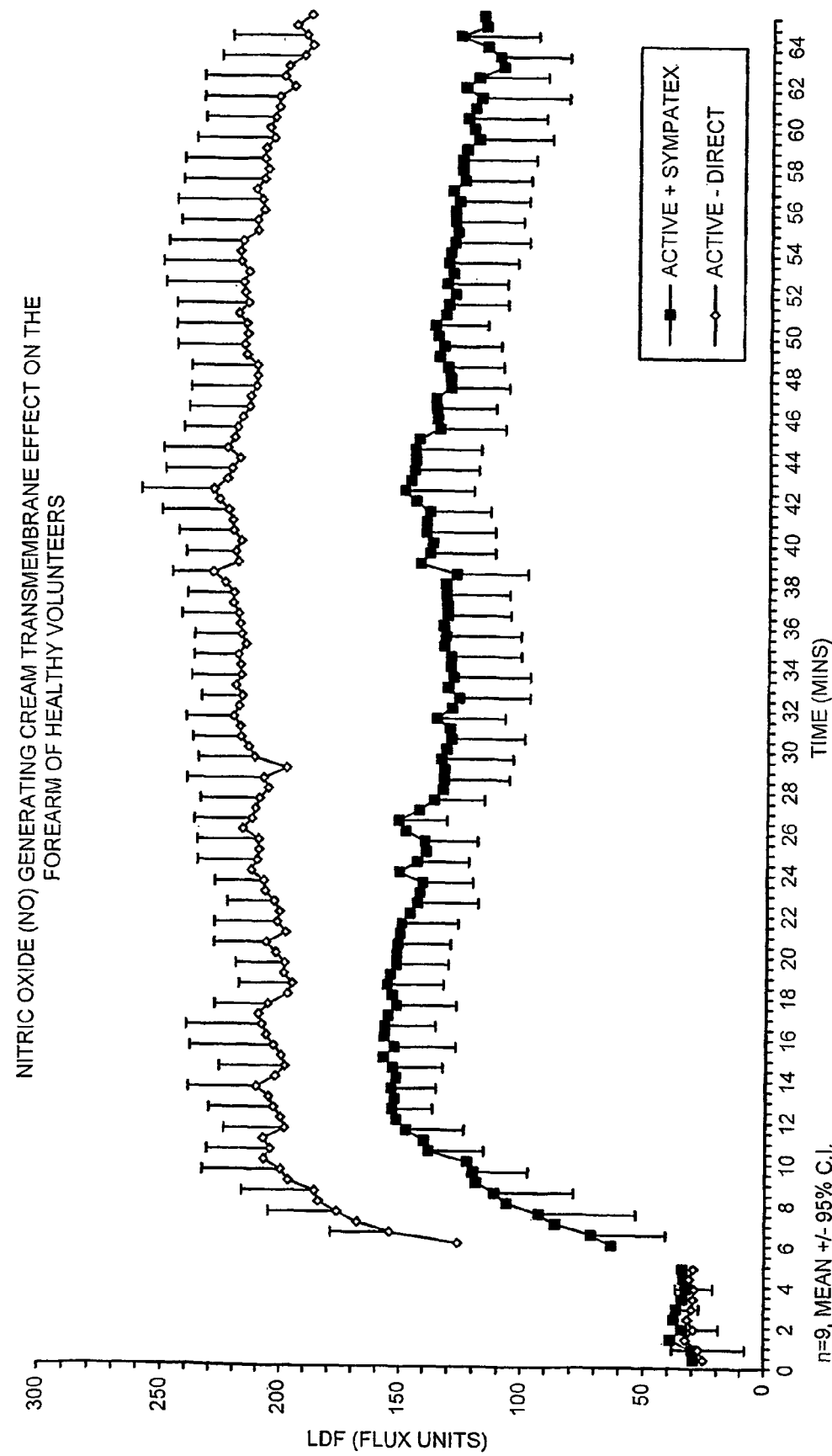
FIG. 7 shows the results of the application of nitric oxide generating gel consisting of 330 mM of sodium nitrite and ascorbic acid in KY Jelly™ to the forearm skin and simultaneously to Sympatex™ 10 μm membrane (Akzo Nobel), which was then applied to the forearm skin of the contralateral limb of nine healthy subjects. Conditions and experimental methods were the same as used for the application of the NO-generation gel on healthy subjects in FIGS. 1, 2, 4 and 5. The vertical axis shows Laser Doppler Fluximetry units and the horizontal axis shows the time in minutes.
Figure 9:
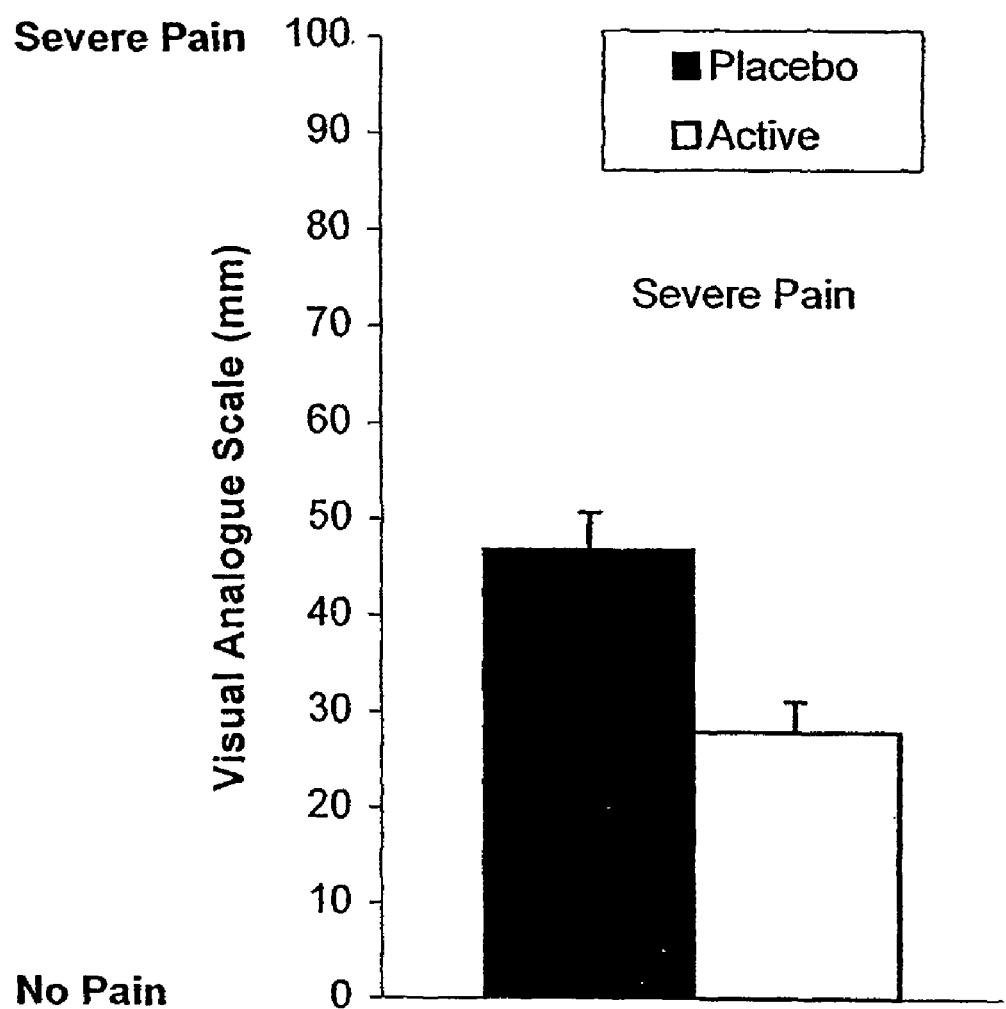
FIG. 9 shows results of Visual Analogue Score (VAS); values are mean±95% CI; n=100; $P<0.001$.

The nitric oxide generating gel consisting of 330 mM of both sodium nitrite and ascorbic acid in KY Jelly™ was applied directly to the forearm skin and simultaneously to Sympatex™ 10 μm membrane (Akzo Nobel), which was then applied to the forearm skin of the contralateral limb if nine healthy subjects. Conditions and experimental methods were the same as used for the application of the NO-generation gel on healthy subjects in FIGS. 1, 2, 4 and 5. The results are shown in FIG. 7. It should be noted that in FIG. 7 that the concentrations of the admixture are in a different unit form (i.e. mM instead of % w/w). Laser Doppler Fluxmetry (LDF) measured the skin microcirculatory flux.

The statistically significant increase in microcirculatory flux from baseline was a reflection of the diffusion of nitric oxide through the membrane towards the skin. This vasodilation, indicated by LDF through the membrane ranged from 60-75% (mean 64%) of that observed when the NO-generation gel was applied directly to the skin of the forearm. The results shown in FIG. 7 support the observations described in FIG. 1 which show that the vasodilator response to the direct treatment reached a plateau phase in all patients within 10 minutes of gel application. A plateau phase, although reduced in amplitude was achieved within 16 minutes when the NO-generation gel was applied to the membrane and reflects a lag phase which is related to membrane diffusion characteristics.

Example 8

Use of a Combined Percutaneous Local Anaesthetic and NO-Generating System for Venepuncture The study was a placebo-controlled double blind trial. The effects of the active and placebo treatment were measured at the same time, applied to different hands. The pain response to cannulation of a dorsal hand vein with a 20G Butterfly™ needle was assessed in one hundred healthy volunteers. The nitric oxide generating system was prepared by mixing two viscous gels. The first was a solution of KY Jelly™ and sodium nitrite (10% w/v) and the second KY Jelly™ and ascorbic acid (10% w/v). This NO-generation gel was termed the placebo treatment, and when combined with lignocaine in aqueous cream to produce a final 5% anaesthetic concentration, active treatment. Approximately 2 ml of the gel mixtures were separately applied to the skin of the dorsum of the hands (3 cm$^2$) for ten minutes. Following successful cannulation pain perception was measured with a verbal rating score (VRS) and a visual analogue score (VAS).

Pilot studies of 2.5-5.0% xylocaine combined with the NO-generating gel applied to the ventral surface of the forearm and the dorsal surface of the hand suggested a significant level of local anaesthesia was achieved within 5-10 minutes as assessed by pin-prick and thermal sensitivity testing. Furthermore, application of xyolcaine directly to the skin failed to produce any discernible level of anaesthesia within 20 minutes. The anaesthetic used in these initial studies was xylocaine as it was readily available in a pharmaceutical form for mixing. The aim of this study was to assess how the nitric oxide generating system previously investigated could be combined with lignocaine to decrease the time of onset and increase the effectiveness of percutaneous anaesthesia?

Materials and Methods

Subjects

The study was a placebo-controlled double blind controlled trial. One hundred healthy, normotensive volunteers were recruited. A medical history was taken including past medical illness, allergies, smoking, alcohol and consumption of other medically active substances. In a physical examination blood pressure, pulse rate and rhythm and signs of drug and alcohol abuse were also recorded.

Exclusion criteria included: analgesia within preceding 24-hour period; known hypersensitivity to anaesthetics; a history of drug allergy, eczema or psoriasis or with cracks or ulceration of the skin near the venepuncture/cannulation site; any significant concomitant disease; pregnancy or breast feeding; volunteers taking any medication with known or potential activity on the cardiovascular system or on blood rheology (for example aspirin or any other NSAID) and blood pressure >160 mmHg systolic or >100 mmHg diastolic.

The study was approved by the East London and City Health Authority Ethics Committee [ELCHA]. Participants were admitted to the investigation having been provided with a verbal and written explanation and signed a consent form.

Methods

The nitric oxide generating system was prepared by mixing two viscous solutions (A and B). Solution A was prepared in KY Jelly™ [Johnson & Johnson Ltd.] a sterile lubricant, to which Analar™ grade sodium nitrite to make a 10% (w/v) gel in a sterile plastic specimen pot. Solution B was prepared by adding Analar grade ascorbic acid (vitamin C) to KY Jelly™ to make a 10% (w/v) gel in a separate sterile plastic pot.

The NO-generation gel was termed the placebo treatment, and when further supplemented with lignocaine in aqueous cream to produce a final 5% anaesthetic concentration, active treatment. The NO-generating gel was used as a placebo treatment because topical application of this system results in a pronounced erythema, which would have prevented effective double blinding of the study. Fresh preparations of gels were prepared for each volunteer. Small quantities (approximately 2.0 ml containing 50 milligrams each of sodium nitrite and ascorbic acid) of active and placebo gel were separately applied to the dorsum of each hand over an area of 3 cm$^2$ and then mixed with a clean cotton bud. Randomisation was performed by computer generated allocation. The active treatment was applied to the dorsal surface of a randomly selected hand and the placebo treatment was simultaneously applied to the contralateral hand. Following 10 minutes of application both hands were cleaned prior to venepuncture.

A vein on each hand within the treatment area was then cannulated using a 20G butterfly needle, performed in accordance with guidelines detailed in the Royal Hospitals NHS Trust *Code of Practice for Phlebotony* with reference to sterility, the risks of infection and contamination. The left hand was cannulated first, followed by the right. The success of cannulation will be recorded by the ability to withdrawal 1 ml of venous blood. If blood was not obtained on the first attempt, then this was counted as a failed procedure and the patient excluded from the study. Following bilateral cannulation, each hand was be cleaned and dressed appropriately.

Efficacy Measurements

Pain perception is subjective and difficult to measure, hence two outcome measures were used. The verbal rating score (VRS) and the visual analogue score (VAS) are well validated criteria (Bradley L. A., *Arthr Care Res*, 178-184 (1993); Woolfson et al *Br J Clin Pharmacol* 30 273-239 (1990)). Each assessment was made using a separate report form without visual reference to previous responses Following successful bilateral cannulation, a VRS pain classification was used with reference first to the left hand, and than repeated for the right hand. The volunteer was asked the following question: "How strong was the pain of the procedure?" and provided with a choice of five answers: [1] No pain; [2] Minimal sensation; [3] Mild pain; [4] Moderate pain; [5] Severe pain (including withdrawal of hand). The volunteer selected one answer for each hand by circling the number.

Severity of pain was also assessed by a VAS, consisting of a 100 mm horizontal line with endpoints that are anchored by descriptors 'No Pain' and 'Severe Pain'. The VAS used with reference first to the left hand, and than the right hand. For each hand the Volunteer was asked the following question "What did the procedure feel like?" and then were requested to make a vertical line across the tramline, which represented the intensity or unpleasantness of his or her pain experienced by the procedure. Values were measured in millimetres from the left of the tramline.

The application of the gels to the volunteer, bilateral cannulation of the dorsal hand veins, and data recording were each performed blindly by separate investigators.

Study Design and Statistical Analysis

The number of patients required to obtain statistical power was difficult to calculate because of the lack of previous studies of this system. However, the uncontrolled pilot study allowed a preliminary power calculations and together with a literature search of similar investigations indicated that one hundred subjects would have an 80% power to detect a difference of 25% in the primary outcome measures at p<0.05. Additionally, assessment of one hundred subjects would reduce the influence of any variability of cannulation procedure.

All volunteers received both active and placebo treatment simultaneously. All analyses and summaries were performed, using Microsoft Excel 5.0a and SPSS 6.1.3 commercially available statistical analysis packages. Comparisons were made between active and placebo treatment. The Verbal Rating Score was categorical/ordinal data, thus non-parametric analysis was used (Fisher's Exact test—an extension of McNemar's test). The Visual Analogue Score data was an interval scale and showed normal distribution as confirmed by Ryan-Joiner probability plots. Therefore parametric analysis was performed using the 2-sample t-test. A P-value of less than 5% was taken to represent statistical significance.

Results

One hundred healthy volunteers were recruited to the study. The demographic data are summarised in Table 1. Additionally, of the one hundred subjects 83 were white European, 8 African/Caribbean, 7 Asian, and 2 Other (Turkish). Forty-four volunteers smoked an average of 5 cigarettes per day (range 1-30) and a further eight had ceased smoking for greater that one month. Eighty-seven volunteers consumed an average of 14 units per week of alcohol (range 1-60 units).

The cannulation procedures were successfully completed at the first attempt for all one hundred volunteers. Tolerance and compliance was high for all subjects. There were no cases of hypersensitivity to either preparation nor adverse event to the investigation.

The verbal rating score (VRS) pain classification recorded significant differences in median scores (FIG. 1). The active treatment (lignocaine+NO-generation system) resulted in a reduced pain response to cannulation than the placebo treatment (NO-generation system alone) (p<0.001). However, seven subjects recorded category [4] Moderate pain for the active treatment representing failure of anaesthesia. Median VRS were similar between the sexes for active and placebo treatments.

The visual analogue score (VAS) were also significantly different between the two groups (FIG. 2). The active treatment resulted in significantly less response to cannulation than the placebo treatment (p<0.001). The active formulation produced a reduction in mean VAS pain score of 40.3%. There were no differences between male and female mean VAS pain scores for either treatment.

TABLE 1

Volunteer demographics

| Parameters | mean ± S.D (range) | median |
|---|---|---|
| sex (Male:Female) | 56:44 | |
| age (years) | 27.6 ± 5.8 (20-40) | 27.0 |
| BMI (weight/height$^2$) | 25.1 ± 4.4 (17.5-42.0) | 24.5 |
| MAP | 89.2 ± 10.0 (69.7-118.7) | 88.7 |
| Heart rate (bpm) | 74 ± 11.5 (54-111) | 74 |

Mean arterial blood pressure [MAP] was calculated as:
Systolic blood pressure−Diastolic blood pressure/3+Diastolic blood pressure Findings Topical application of the NO-generating gel and lignocaine mixture significantly reduced the pain associated with venous cannulation. The formulation resulted in a decreased VRS (p<0.0001) and produced a reduction in mean VAS of >40% compared to the placebo gel (P<0.001).

Interpretation

This investigation suggests that topical application for ten minutes of the combination of anaesthetic with a nitric oxide-generation system may provided effective anaesthesia for venous cannulation in adults. No adverse effects were reported with this treatment.

Discussion

This study suggests that a ten-minute topical application of the combination of lignocaine with a nitric oxide-generation system may provide effective anaesthesia for venous cannulation of the dorsum of the hand in adults. These findings are important as cannulation of the dorsal hand vein is commonly described as a painful procedure in comparison to other anatomical regions. The degree of anaesthesia observed was achieved following only ten minutes of application. This is not the case for existing commercially available treatments.

The main route for a drug molecule penetrating the stratum cornuem is through the intercellular matrix while very limited drug penetration occurs via the intracellular corneocytes (Singh S, and Singh J. *Med Res Rev* 13 (5), pages 569-621 (1993)). Additionally, drugs may enter the skin through specialised structures such as sweat ducts and hair follicles. The influence of the NO-generation system on the route of lignocaine transmission is unclear at this time and awaits elaboration, but may be related to increased cutaneous blood flow.

Although other investigators using EMLA™ and Ametop Gel™ report variable levels of erythema dependent upon the duration of application (Arrowsmith J, and Campbell C. *Arch Dis Child* 82(4) pages 309-310 (2000)), clinical experience suggests that they do significantly effect the tone of the venous vessels. The nitric oxide component of this system results in an increase in luminal diameter (consequent to vasodilatation) and the apparent attenuation of vasospasm may assist in the cannulation of small, vasospastic or friable vessels.

A further observation in the treatment area with an associated increase in the colour contrast between the blue venous vessels and the red erythema of the skin. The delineated area of gel application facilitated the identification of the region of treatment and targeting of the vein by the clinician. The erythema was transient in nature and was not associated with tissue oedema.

The ideal percutaneous local anaesthetic preparation will need to fulfil a number of requirements [a] To profoundly anaesthetise the skin surface and underlying tissues; [b] Have a more rapid onset of action; [c] Increase vasodilation of venous vessels; [d] Have a prolonged duration of action; [e] Contain the minimum necessary concentration of local anaesthetic; [f] Produce no systemic toxicity; [g] Produce no significant local reactions; [h] Avoids sensitisation to future skin application. The formulation described in this study appears to have the potential to fulfil these criteria.

This investigation is a preliminary report. However, the findings of this study suggest that future studies are required to investigate the effects of anaesthetic type, formulation and concentration, duration of action and penetration depth, anatomical and physiological variation and comparisons with both EMLA™ and Ametop Gel™. A further interesting possibility exists that the nitric oxide-generation gel may not be a true placebo and may in fact have some degree of anaesthetic effect (Redford et al *Brain* 120 (12), pages 2149-2157 (1997); Sousa A M, and Prado W A., *Brain Res* 897(1-2), pages 9-19 (2001)). However, if demonstrated this effect would clearly add to the efficacy of the combined system as a topically-applied anaesthesia.

In summary, this investigation is believed to be the first to describe the addition of a primary pharmaceutical agent with a topically-applied nitric oxide generation system. The combined system may overcome the limitations associated with conventional transdermal drug application and be developed into a clinically useful transdermal delivery technology for a broad spectrum of pharmaceutical agents.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

The invention claimed is:

1. A topically-applied, nitric oxide (NO)-generating system for providing rapid transdermal delivery of a pharmaceutically-active agent to a patient in need thereof, the system consisting of a pharmacologically-acceptable acidifier in aqueous combination with a nitrite selected from the group consisting of an alkali metal nitrite, an alkaline earth metal nitrite, and a nitrite precursor therefor, wherein when the pharmaceutically active agent is topically applied at the site of the NO-generating system on the patient's skin, the NO-generating system operates to transdermally deliver to the patient within <10 minutes from the time of application, an amount of the pharmaceutically-active agent that is sufficient to achieve a statistically significantly greater response to the pharmaceutically-active agent in the patient than the response achieved by application of the pharmaceutically-active agent alone.

2. The transdermal delivery system of claim 1, wherein the nitrite concentration ranges from about 2% to 10%.

3. The transdermal delivery system of claim 1, wherein the pharmaceutically-active agent applied therewith comprises an anaesthetic or an analgesic, or combinations thereof.

4. The transdermal delivery system of claim 1, wherein the pharmacologically-acceptable acidifier comprises an organic acid.

5. The transdermal delivery system of claim 4, wherein the organic acid is selected from the group consisting of ascorbic acid, salicylic acid, acetyl salicylic acid, a ($C_1$-$C_6$) alkyl carboxylic acid, a ($C_6$-$C_{10}$) aryl ($C_1$-$C_6$) carboxylic acid, citric acid, and a salt or derivative thereof.

6. The transdermal delivery system of claim 3, wherein the NO-generating system operates to transdermally deliver an active agent comprising an anaesthetic selected from the group consisting of amethocaine (tetracaine), lignocaine (lidocaine), xylocalne, bupivacaine, prilocalne, ropivacaine, benzocaine, mepivocaine, cocaine and combinations thereof.

7. The transdermal delivery system of claim 1, wherein the final nitrite ion concentration comprises up to 20%.

8. The transdermal delivery system of claim 1, wherein the NO-generating system operates to transdermally deliver to the patient within ≦5 minutes from the time of application, the amount of the pharmaceutically-active agent that is sufficient to achieve the statistically significantly greater response to the pharmaceutically-active agent in the patient than the response achieved by application of the pharmaceutically-active agent alone.

9. The transdermal delivery system of claim 1, wherein the pharmacologically-acceptable acidifier is selected from the group consisting of dilute hydrochloric acid, betaine hydrochloride, acetic acid, citric acid, citric acid monohydrate, fumaric acid, lactic acid, maleic acid, malic acid, tartaric acid, hexose or pentose sugar molecules substituted with a ($C_1$-$C_6$) carboxyl group, furanolactone or pyranolactone molecules substituted with a ($C_1$-$C_6$) carboxyl group, ammonium salts, aluminum salts, phenol, benzoic acid and other ($C_6$-$C_{10}$) aryl compounds, and derivatives thereof.

10. The transdermal delivery system of claim 3, wherein the NO-generating system operates to transdermally deliver an active agent comprising an analgesic selected from the group consisting of ibuprofen, acetylsalicylic acid, paracetamol, metoprolol, and oxycodone, and combinations thereof.

11. The transdermal delivery system of claim 1, wherein the nitrite ions provided by alkali metal nitrite or, alkaline earth metal nitrite, or nitrite precursor are selected from the group consisting of $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, $Ra(NO_2)_2$, and dilute solutions of nitrous acid, or nitrite ions are provided by enzymatic conversion from alkali metal nitrite or alkaline earth metal nitrite, selected from the group consisting of $LiNO_3$, $NaNO_3$, $KNO_3$, $RbNO_3$, $CsNO_3$, $FrNO_3$, $Be(NO_3)_2$, $Mg(NO_3)_2$, $Ca(NO_3)_2$, $Sr(NO_3)_2$, $Ba(NO_3)_2$ and $Ra(NO_3)_2$.

12. A topically-applied, nitric oxide (NO)-generating system for providing rapid transdermal delivery of a pharmaceutically-active agent to a patient in need thereof, the system consisting of a pharmacologically-acceptable acidifier in aqueous combination with a nitrite selected from the group consisting of an alkali metal nitrite, an alkaline earth metal nitrite, and a nitrite precursor therefor, in combination with a water-based, pharmacologically-acceptable carrier or diluent, or combination thereof, wherein when the pharmaceutically active agent is topically applied at the site of the NO-generating system on the patient's skin, the NO-generating system operates to transdermally deliver to the patient within <10 minutes from the time of application, an amount of the pharmaceutically-active agent that is sufficient to achieve a statistically significantly greater response to the pharmaceutically-active agent in the patient than the response achieved by application of the pharmaceutically-active agent alone.

13. The transdermal delivery system of claim 12, wherein the nitrite concentration ranges from about 2% to 10%.

14. The transdermal delivery system of claim 12, wherein the pharmaceutically-active agent applied therewith comprises an anaesthetic or an analgesic, or combinations thereof.

15. The transdermal delivery system of claim 12, wherein the pharmacologically-acceptable acidifier comprises an organic acid.

16. The transdermal delivery system of claim 15, wherein the organic acid is selected from the group consisting of ascorbic acid, salicylic acid, acetyl salicylic acid, a ($C_1$-$C_6$) alkyl carboxylic acid, a ($C_6$-$C_{10}$) aryl ($C_1$-$C_6$) carboxylic acid, citric acid, and a salt or derivative thereof.

17. The transdermal delivery system of claim 14, wherein the NO-generating system operates to transdermally deliver an active agent comprising an anaesthetic selected from the group consisting of amethocaine (tetracaine), lignocaine (lidocaine), xylocalne, bupivacaine, prilocalne, ropivacaine, benzocaine, mepivocaine, cocaine and combinations thereof.

18. The transdermal delivery system of claim 12, wherein the final nitrite ion concentration comprises up to 20%.

19. The transdermal delivery system of claim 12, wherein the NO-generating system operates to transdermally deliver to the patient within ≦5 minutes from the time of application, the amount of the pharmaceutically-active agent that is sufficient to achieve the statistically significantly greater response to the pharmaceutically-active agent in the patient than the response achieved by application of the pharmaceutically-active agent alone.

20. The transdermal delivery system of claim 12, wherein the pharmacologically-acceptable acidifier is selected from the group consisting of dilute hydrochloric acid, betaine hydrochloride, acetic acid, citric acid, citric acid monohydrate, fumaric acid, lactic acid, maleic acid, malic acid, tartaric acid, hexose or pentose sugar molecules substituted with a ($C_1$-$C_6$) carboxyl group, furanolactone or pyranolactone molecules substituted with a ($C_1$-$C_6$) carboxyl group, ammonium salts, aluminum salts, phenol, benzoic acid and other ($C_6$-$C_{10}$) aryl compounds, and derivatives thereof.

21. The transdermal delivery system of claim 14, wherein the NO-generating system operates to transdermally deliver an active agent comprising an analgesic selected from the group consisting of ibuprofen, acetylsalicylic acid, paracetamol, metoprolol, and oxycodone, and combinations thereof.

22. The transdermal delivery system of claim 12, wherein the nitrite ions provided by alkali metal nitrite or, alkaline earth metal nitrite, or nitrite precursor are selected from the group consisting of $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, $Ra(NO_2)_2$, and dilute solutions of nitrous acid, or nitrite ions are provided by enzymatic conversion from alkali metal nitrite or alkaline earth metal nitrite, selected from the group consisting of $LiNO_3$, $NaNO_3$, $KNO_3$, $RbNO_3$, $CsNO_3$, $FrNO_3$, $Be(NO_3)_2$, $Mg(NO_3)_2$, $Ca(NO_3)_2$, $Sr(NO_3)_2$, $Ba(NO_3)_2$ and $Ra(NO_3)_2$.

* * * * *